(12) United States Patent
Kaneko et al.

(10) Patent No.: US 9,301,725 B2
(45) Date of Patent: Apr. 5, 2016

(54) RADIATION IMAGE CAPTURING SYSTEM

(71) Applicant: Konica Minolta, Inc., Tokyo (JP)

(72) Inventors: Shikou Kaneko, Tokorozawa (JP); Yuuichi Maruta, Hino (JP)

(73) Assignee: KONICA MINOLTA, INC. (JP)

( * ) Notice: Subject to any disclaimer, the term of this patent is extended or adjusted under 35 U.S.C. 154(b) by 111 days.

(21) Appl. No.: 14/068,778

(22) Filed: Oct. 31, 2013

(65) Prior Publication Data

US 2014/0119509 A1 May 1, 2014

(30) Foreign Application Priority Data

Oct. 31, 2012 (JP) ................................ 2012-239783

(51) Int. Cl.
*A61B 6/00* (2006.01)

(52) U.S. Cl.
CPC .............. *A61B 6/4233* (2013.01); *A61B 6/4283* (2013.01); *A61B 6/54* (2013.01); *A61B 6/544* (2013.01)

(58) Field of Classification Search
CPC ...... G01T 1/24; G01T 1/2992; A61B 6/4233; A61B 6/54; A61B 6/4283; A61B 6/544
USPC .......................................................... 378/62
See application file for complete search history.

(56) References Cited

U.S. PATENT DOCUMENTS

| | | | |
|---|---|---|---|
| 7,211,803 B1 | 5/2007 | Dhurjaty et al. | |
| 2003/0016854 A1* | 1/2003 | Inoue et al. | 382/132 |
| 2009/0034679 A1* | 2/2009 | Okamura | 378/19 |
| 2009/0123051 A1* | 5/2009 | Tamai et al. | 382/132 |
| 2012/0018646 A1* | 1/2012 | Takahashi | 250/370.09 |
| 2012/0091352 A1* | 4/2012 | Enomoto | 250/370.08 |
| 2012/0112081 A1* | 5/2012 | Tajima | 250/370.08 |
| 2013/0243301 A1* | 9/2013 | Sakaguchi et al. | 382/132 |

FOREIGN PATENT DOCUMENTS

| | | |
|---|---|---|
| JP | 06-342099 A | 12/1994 |
| JP | 09-073144 A | 3/1997 |
| JP | 2006-058124 A | 3/2006 |

(Continued)

OTHER PUBLICATIONS

Japanese Notification of Reasons for Refusal corresponding to Application No. 2012-239783; Date of Mailing: Jan. 26, 2016, with English translation.

*Primary Examiner* — Glen Kao
(74) *Attorney, Agent, or Firm* — Cantor Colburn LLP

(57) ABSTRACT

A radiation image capturing system includes a radiation image capturing apparatus, one or more radiation generation apparatuses and a calculation unit. The radiation image capturing apparatus includes a control unit which controls a scan driving unit and a readout integrated circuit of the radiation image capturing apparatus since before start of irradiation of the radiation image capturing apparatus and detects the start of the irradiation when data read out by the readout integrated circuit is equal to or more than a threshold. Before radiation image capturing, the calculation unit calculates a maximum body thickness for each of the radiation generation apparatuses on the basis of the data read out in the radiation image capturing apparatus irradiated by the radiation generation apparatus, the maximum body thickness up to which the control unit can detect the start of the irradiation through a subject.

13 Claims, 15 Drawing Sheets

(56) References Cited

FOREIGN PATENT DOCUMENTS

| | | |
|---|---|---|
| JP | 2009-219538 A | 10/2009 |
| JP | 2012-143472 A | 8/2012 |
| JP | 2012143472 A | 8/2012 |
| WO | 2011135917 A1 | 11/2011 |
| WO | 2011152093 A1 | 12/2011 |

\* cited by examiner

| SENSITIVITY | FIRST TIME | SECOND TIME | THIRD TIME | RESULT |
|---|---|---|---|---|
| HIGH | O | × | × | UNUSABLE |
| MEDIUM | O | × | O | UNUSABLE |
| LOW | O | O | O | USABLE |

RADIATION IMAGE CAPTURING SYSTEM

The present invention claims priority under 35 U.S.C. §119 to Japanese Application No. 2012-239783 filed Oct. 31, 2012, the entire content of which is incorporated herein by reference.

BACKGROUND OF THE INVENTION

1. Field of the Invention

The present invention relates to a radiation image capturing system, and in particular, relates to a radiation image capturing system which uses a radiation image capturing apparatus to perform radiation image capturing in a radiography room.

2. Description of the Related Art

Various kinds of the so-called direct-type radiation image capturing apparatus and the so-called indirect-type radiation image capturing apparatus have been developed. The direct-type radiation image capturing apparatus generates electric charges using detection elements according to the radiation dose of, for example, received X-rays and converts the electric charges into electric signals. The indirect-type radiation image capturing apparatus first converts received radiation into electromagnetic waves of another wavelength such as visible light by using, for example, a scintillator, generates electric charges according to the amount of energy of the converted electromagnetic waves using photoelectric conversion elements such as photodiodes and then converts the electric charges into electric signals (i.e. image data). In the present invention, the detection elements of the direct-type radiation image capturing apparatus and the photoelectric conversion elements of the indirect-type radiation image capturing apparatus are collectively called radiation detection elements.

Radiation image capturing apparatuses of these types are known as FPD (Flat Panel Detector), and each used to be formed integrally with a support (or Bucky device) and called by such a name as a specialized-type (for example, refer to Japanese Patent Application Laid-Open Publication No. hei 09-73144). Recently, portable radiation image capturing apparatuses of these types made by placing radiation detection elements and other parts in a housing have been developed and put into practical use (for example, refer to Japanese Patent Application Laid-Open Publication No. 2006-058124 or Japanese Patent Application Laid-Open Publication No. hei 06-342099).

As shown in, for example, FIG. 2 or 3 described below, in these radiation image capturing apparatuses, normally radiation detection elements 7 are arranged two-dimensionally (in a matrix) over a detection unit P, and switch elements constituted of thin film transistors (hereinafter referred to as TFTs) 8 are connected to the radiation detection elements 7 one-to-one.

Usually, radiation image capturing is performed by a radiation generation apparatus 55 (see FIG. 4 described below) irradiating (i.e. emitting radiation to) a radiation image capturing apparatus through a predetermined radiography part of the body of a subject (front chest or lateral lumbar, for example).

At the time, the radiation is emitted in a state in which OFF voltage is applied to lines L1 to Lx of scan lines 5 from a gate driver 15b of a scan driving unit 15 of the radiation image capturing apparatus to set all the TFTs 8 to an OFF state (an electric charge accumulation state described below). Accordingly, the electric charges generated in the radiation detection elements 7 are accumulated therein for sure by the irradiation.

After the electric charge accumulation state, ON voltage is sequentially applied to the lines L1 to Lx of the scan lines 5 from the gate driver 15b to sequentially set the TFTs 8 to an ON state, and the electric charges generated in the radiation detection elements 7 and accumulated therein by the irradiation are sequentially released to signal lines 6 and read out as image data D by readout circuits 17, whereby an image data D readout process is performed.

In order to appropriately perform radiation image capturing, it is necessary that when the radiation image capturing apparatus is irradiated, OFF voltage is appropriately applied to the lines L1 to Lx of the scan lines 5 from the gate driver 15b to set the TFTs 8 as the switch elements to the OFF state.

Hence, for example, a conventional specialized-type radiation image capturing apparatus is often configured to build an interface between the radiation image capturing apparatus and a radiation generation apparatus so as to send/receive signals or the like to/from the radiation generation apparatus, and make the radiation generation apparatus emit radiation to the radiation image capturing apparatus after applying OFF voltage to the lines L1 to Lx of the scan lines 5 and then confirming that the radiation image capturing apparatus is in the electric charge accumulation state.

However, for example, when manufactures of a radiation image capturing apparatus and a radiation generation apparatus are different, it is not always easy to build an interface between the radiation image capturing apparatus and the radiation generation apparatus or it may be impossible to build the interface.

In the case of no interface between a radiation image capturing apparatus and a radiation generation apparatus, the radiation image capturing apparatus cannot know the timing at which the radiation generation apparatus emits radiation thereto. Therefore, the radiation image capturing apparatus itself needs to detect that the radiation is emitted from the radiation generation apparatus, namely, itself needs to detect irradiation thereof by the radiation generation apparatus.

Then, various kinds of such radiation image capturing apparatuses each configured to itself detect start of irradiation thereof have been developed with no interface between the radiation image capturing apparatus and a radiation generation apparatus.

For example, there is described in U.S. Pat. No. 7,211,803 or Japanese Patent Application Laid-Open Publication No. 2009-219538 that when irradiation of a radiation image capturing apparatus starts, electric charges are generated in radiation detection elements 7, the generated electric charges flow out from the radiation detection elements 7 into bias lines 9 (see FIG. 2 or 3 described below) connected thereto, and the amount of current flowing in the bias lines 9 increases. Then, it is proposed therein that the bias lines 9 are provided with a current detection unit to detect the current value of the current flowing in the bias lines 9, and start of irradiation thereof or the like is detected on the basis of the current value.

However, according to the studies of the inventors of the present invention et al., it has been found that the above method has some problems which cannot be solved easily. One of the problems is that because the bias lines 9 are connected to electrodes of the radiation detection elements 7, the noise generated in the current detection unit is transmitted to the radiation detection elements 7 via the bias lines 9, and the noise is superimposed on the image data D read out from the radiation detection elements 7.

The inventors of the present invention et al. carried out various studies to find alternative methods for detecting irradiation with a radiation image capturing apparatus itself, and succeeded in finding several methods which enable accurate detection of start of irradiation with a radiation image capturing apparatus itself (refer to International Publication No. WO 2011/135917 or International Publication No. WO 2011/152093).

By the way, as described in Japanese Patent Application Laid-Open Publication No. 2012-143472, in the case where a radiation image capturing apparatus itself detects start of irradiation thereof, it is necessary that parameters for the processes performed by the radiation image capturing apparatus are appropriately adjusted, and sensitivity to detect start of irradiation thereof is adjusted to a level at which start of irradiation thereof can be accurately detected. It is known that the sensitivity also depends on the irradiation characteristic of a radiation generation apparatus which irradiates the radiation image capturing apparatus.

According to the studies of the inventors of the present invention et al., it has also been found that there is a case where the sensitivity is adjusted as described above, and a radiation image capturing apparatus itself can accurately detect start of irradiation thereof by a radiation generation apparatus when radiation image capturing of the front chest of a certain subject (i.e. a patient or the like) is performed in a certain radiography room, but the radiation image capturing apparatus cannot accurately detect start of irradiation thereof when the subject is moved to another radiography room and radiation image capturing of the front chest of the subject is performed in that radiography room.

Further, even in the same radiography room, when a radiation generation apparatus which irradiates the radiation image capturing apparatus is replaced by another, as with the case described above, the following may occur; a radiation image capturing apparatus can accurately detect start of irradiation thereof when a radiation generation apparatus irradiates the radiation image capturing apparatus, but the radiation image capturing apparatus cannot detect start of irradiation thereof when another radiation generation apparatus irradiates the radiation image capturing apparatus.

Further, for example, when a radiation image capturing apparatus is taken to a patient's room where a patient is hospitalized or a home of a patient, and radiation image capturing is performed therein by a portable radiation generation apparatus irradiating the radiation image capturing apparatus, the following may occur; a radiation image capturing apparatus can detect start of irradiation thereof in a radiography room of a hospital, but the radiation image capturing apparatus cannot detect start of irradiation thereof in a patient's room of a hospital or the like and cannot appropriately perform radiation image capturing.

Thus, according to the studies of the inventors of the present invention et al., it has been found that whether or not a radiation image capturing apparatus can detect start of irradiation thereof depends on radiation generation apparatuses.

When a radiation image capturing apparatus cannot detect start of irradiation thereof although a radiation generation apparatus irradiates the radiation image capturing apparatus through a subject, the radiation image capturing apparatus cannot move to the electric charge accumulation state or the image data D readout process. Consequently, the radiation image capturing apparatus needs, for example, to increase its sensitivity to detect start of irradiation thereof, and then radiation needs to be emitted to the same subject again to capture a radiation image of the subject.

It means that the first time's irradiation is a waste. In addition, the exposed dose to the subject unnecessarily increases, and accordingly burden is unnecessarily imposed on the subject. Further, operability of the radiation image capturing system decreases, such as usability of the radiation image capturing system including the radiation image capturing apparatus and the radiation generation apparatus for operators such as radiologists (hereinafter "operator(s)") decreases.

BRIEF SUMMARY OF THE INVENTION

The present invention is made by taking the above-mentioned problems into consideration, and an object of the present invention is to provide a radiation image capturing system in which a radiation image capturing apparatus can accurately detect start of irradiation thereof and appropriately perform radiation image capturing even when a radiation generation apparatus which irradiates the radiation image capturing apparatus is replaced by another.

Another object of the present invention is to provide a radiation image capturing system in which even when a radiography condition changes, for example, a radiation generation apparatus is replaced by another, a radiation image capturing apparatus can appropriately perform radiation image capturing by appropriately changing its state in accordance with the change of the radiography condition.

According to the studies of the inventors of the present invention et al., it has also been found that there is a case where a radiation image capturing apparatus falsely detects start of irradiation thereof although the radiation image capturing apparatus is not actually irradiated because of the influence of, for example: radio waves emitted from an apparatus or the like in a radiography room; impacts, vibrations or the like added to the radiation image capturing apparatus from an apparatus used for radiation image capturing; or impacts, vibrations or the like added to the radiation image capturing apparatus by a patient hitting himself/herself against the radiation image capturing apparatus.

When such false detection occurs, an operator needs to stop the radiation image capturing apparatus from moving to the electric charge accumulation state or each process such as the image data D readout process which the radiation image capturing apparatus is performing after false detection, and return the radiation image capturing apparatus to an irradiation start detection state, and then radiation image capturing needs to be performed again.

Thus, once false detection occurs, an operator needs to perform such troublesome processes described above. Also, false detection delays the timing at which radiation image capturing is performed. Thus, radiation image capturing cannot be performed smoothly. In addition, a patient who is a subject for radiation image capturing needs to wait until the above described processes are completed. Accordingly, usability of the radiation image capturing system decreases.

Therefore, another object of the present invention is to provide a radiation image capturing system in which a condition which enables radiation image capturing with a radiation image capturing apparatus is found in advance, and the radiation image capturing apparatus is appropriately adjusted to perform radiation image capturing in accordance with an operating environment where the radiation image capturing apparatus is used.

In order to achieve at least one of the objects, according to a first aspect of the present invention, there is provided a radiation image capturing system including: a radiation image capturing apparatus including: a plurality of scan lines; a plurality of signal lines disposed to intersect with the scan lines; a plurality of radiation detection elements disposed two-dimensionally; a scan driving unit which applies ON voltage and OFF voltage to the scan lines, switching the ON voltage and the OFF voltage; a plurality of switch elements which are connected to the scan lines and release electric charges accumulated in the radiation detection elements to the signal lines when the ON voltage is applied to the switch elements via the scan lines; a readout integrated circuit which reads out the electric charges released from the radiation detection elements as image data; and a control unit which controls the scan driving unit and the readout integrated circuit since before start of irradiation of the radiation image capturing apparatus and detects the start of the irradiation when data read out by the readout integrated circuit is equal to or more than a threshold; and one or more radiation generation apparatuses each of which irradiates the radiation image capturing apparatus; and a calculation unit which, before radiation image capturing, calculates a maximum body thickness for each of the radiation generation apparatuses on the basis of the data read out in the radiation image capturing apparatus irradiated by the radiation generation apparatus, the maximum body thickness up to which the control unit can detect the start of the irradiation through a subject.

In order to achieve at least one of the objects, according to a second aspect of the present invention, there is provided a radiation image capturing system including: a radiation image capturing apparatus including: a plurality of scan lines; a plurality of signal lines disposed to intersect with the scan lines; a plurality of radiation detection elements disposed two-dimensionally; a scan driving unit which applies ON voltage and OFF voltage to the scan lines, switching the ON voltage and the OFF voltage; a plurality of switch elements which are connected to the scan lines and release electric charges accumulated in the radiation detection elements to the signal lines when the ON voltage is applied to the switch elements via the scan lines; a readout integrated circuit which reads out the electric charges released from the radiation detection elements as image data; and a control unit which controls the scan driving unit and the readout integrated circuit since before start of irradiation of the radiation image capturing apparatus and detects the start of the irradiation when data read out by the readout integrated circuit is equal to or more than a threshold; and a radiation generation apparatus which irradiates the radiation image capturing apparatus; and a console which controls the radiation image capturing apparatus and the radiation generation apparatus, wherein the control unit changes sensitivity of the control unit for an irradiation start detection process to detect the start of the irradiation, and the console sends a signal to change the sensitivity to the radiation image capturing apparatus.

In order to achieve at least one of the objects, according to a third aspect of the present invention, there is provided a radiation image capturing system including: a radiation image capturing apparatus including: a plurality of scan lines; a plurality of signal lines disposed to intersect with the scan lines; a plurality of radiation detection elements disposed two-dimensionally; a scan driving unit which applies ON voltage and OFF voltage to the scan lines, switching the ON voltage and the OFF voltage; a plurality of switch elements which are connected to the scan lines and release electric charges accumulated in the radiation detection elements to the signal lines when the ON voltage is applied to the switch elements via the scan lines; a readout integrated circuit which reads out the electric charges released from the radiation detection elements as image data; and a control unit which controls the scan driving unit and the readout integrated circuit since before start of irradiation of the radiation image capturing apparatus and detects the start of the irradiation when data read out by the readout integrated circuit is equal to or more than a threshold; and a radiation generation apparatus which irradiates the radiation image capturing apparatus, wherein the control unit of the radiation image capturing apparatus changes sensitivity of the control unit for an irradiation start detection process to detect the start of the irradiation by changing the threshold, and the radiation image capturing system further comprises a determination unit which, before radiation image capturing, determines whether or not the control unit can detect the start of the irradiation at each of sensitivity levels of the sensitivity on the basis of the data read out in the radiation image capturing apparatus not irradiated by the radiation generation apparatus and notifies a result of the determination.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein:

FIG. 4 shows a configuration example of a radiation image capturing system according to embodiments of the present invention built in a radiography room and the like;

FIG. 5 shows a configuration example of the radiation image capturing system according to the embodiments built on a nursing cart and the like;

DETAILED DESCRIPTION OF THE INVENTION

In the following, embodiments of a radiation image capturing system according to the present invention are described with reference to the drawings.

In the following, as a radiation image capturing apparatus used in the radiation image capturing system, the so-called indirect-type radiation image capturing apparatus is described. The indirect-type radiation image capturing apparatus includes a scintillator and obtains electric signals by converting radiation with which the radiation image capturing apparatus is irradiated into electromagnetic waves of another wavelength such as visible light. The present invention can also be applied to the so-called direct-type radiation image capturing apparatus which directly detects the radiation with radiation detection elements without using a scintillator or the like.

Although the radiation image capturing apparatus described herein is the so-called portable-type, the present invention can also be applied to the so-called specialized-type radiation image capturing apparatus which is formed integrally with a support or the like.

[Radiation Image Capturing Apparatus]

Figure 1:
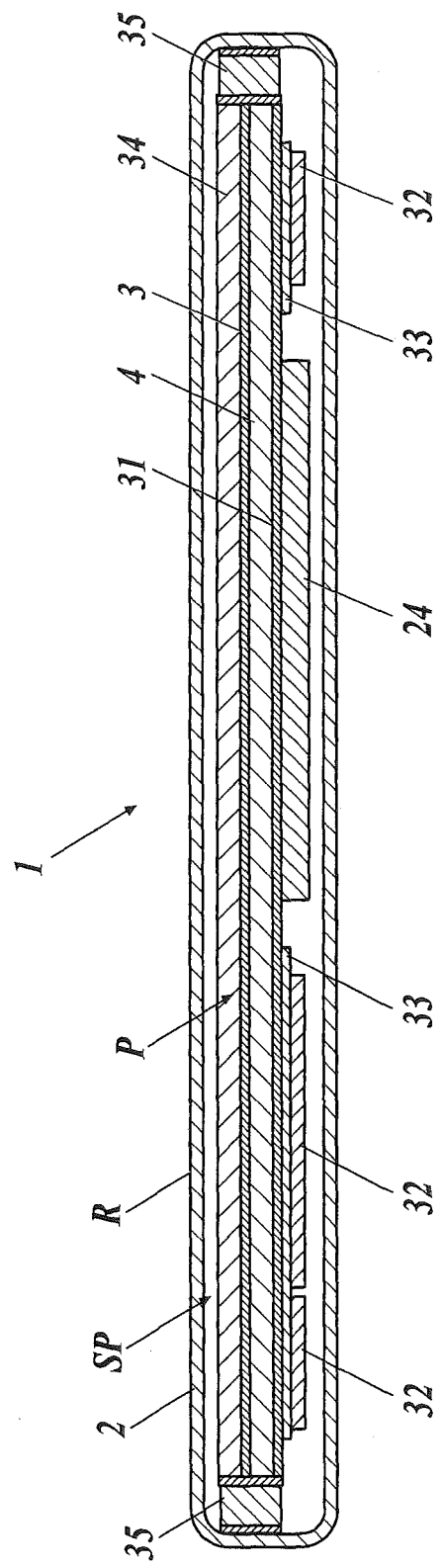
FIG. 1 is a sectional view of a radiation image capturing apparatus.
Figure 2:
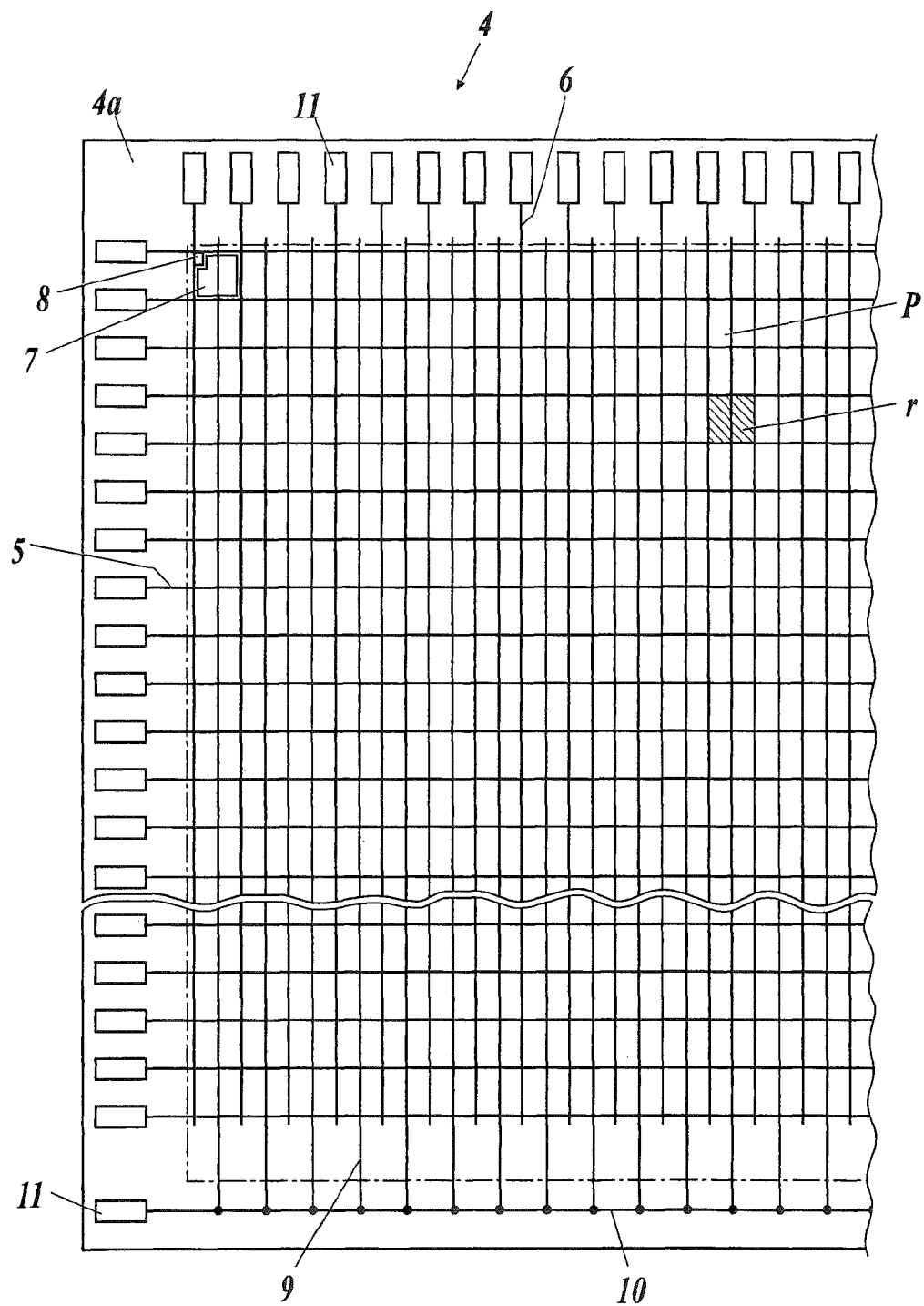
FIG. 2 is a plan view showing the configuration of a circuit board of the radiation image capturing apparatus.

First, the configuration and the like of the radiation image capturing apparatus used in the radiation image capturing system according to the embodiments of the present invention are described. FIG. 1 is a sectional view of the radiation image capturing apparatus according to the embodiments, and FIG. 2 is a plan view showing the configuration of a circuit board in the radiation image capturing apparatus.

As shown in FIG. 1, a radiation image capturing apparatus 1 includes: a housing 2 made of a carbon board or the like and having a radiation incidence surface R as a surface on a side which is irradiated; and a sensor panel SP placed in the housing 2. The sensor panel SP includes a scintillator 3 and a circuit board 4. In addition, although omitted in FIG. 1, in the embodiments, the housing 2 is provided with an antenna device 41 (see FIG. 3 described below) as a wireless communication unit which transfers the image data D and the like to a console 58 described below (see FIG. 4 or 5 described below) by wireless transmission.

Although omitted in FIG. 1, in the embodiments, the radiation image capturing apparatus 1 includes a connecter disposed on a lateral surface or the like of the housing 2 so that signals, data and the like can be transferred to, for example, the console 58 via the connecter by wire transmission. This connecter functions as a wired communication unit of the radiation image capturing apparatus 1.

As shown in FIG. 1, a base 31 is disposed in the housing 2, and the circuit board 4 is disposed on the radiation incidence surface R side of the base 31 (hereinafter simply referred to as the upper surface side) with, for example, a not-shown lead sheet placed between the base 31 and the circuit board 4. On the upper surface side of the circuit board 4, the scintillator 3 which converts received radiation into light such as visible light is disposed on a scintillator circuit board 34, facing the circuit board 4.

On the other hand, PCBs 33, a battery 24 and the like are attached to the lower surface of the base 31. Electronic parts 32 and the like are mounted on the PCBs 33. The sensor panel SP is thus constituted of the base 31, the circuit board 4 and the like. In addition, cushions 35 are disposed in the spaces between the sensor panel SP and the lateral surfaces of the housing 2 in the embodiments.

The circuit board 4 is made of a glass substrate in the embodiments. As shown in FIG. 2, a plurality of scan lines 5 and a plurality of signal lines 6 are arranged on the upper surface 4a (i.e. the surface facing the scintillator 3) of the circuit board 4 in such a way that the scan lines 5 and the signal lines 6 intersect with each other. A radiation detection element 7 is disposed in each of the small regions r defined by the scan lines 5 and the signal lines 6 on the upper surface 4a of the circuit board 4.

Thus, the whole of the small regions r in which the radiation detection elements 7 are arranged two-dimensionally (in a matrix), one radiation detection element 7 in each one of the small regions r defined by the scan lines 5 and the signal lines 6, forms a detection unit P, which is the region defined by the dashed line in FIG. 2. Although photodiodes are used as the radiation detection elements 7 in the embodiments, for example, phototransistors may be used instead.

Figure 3:
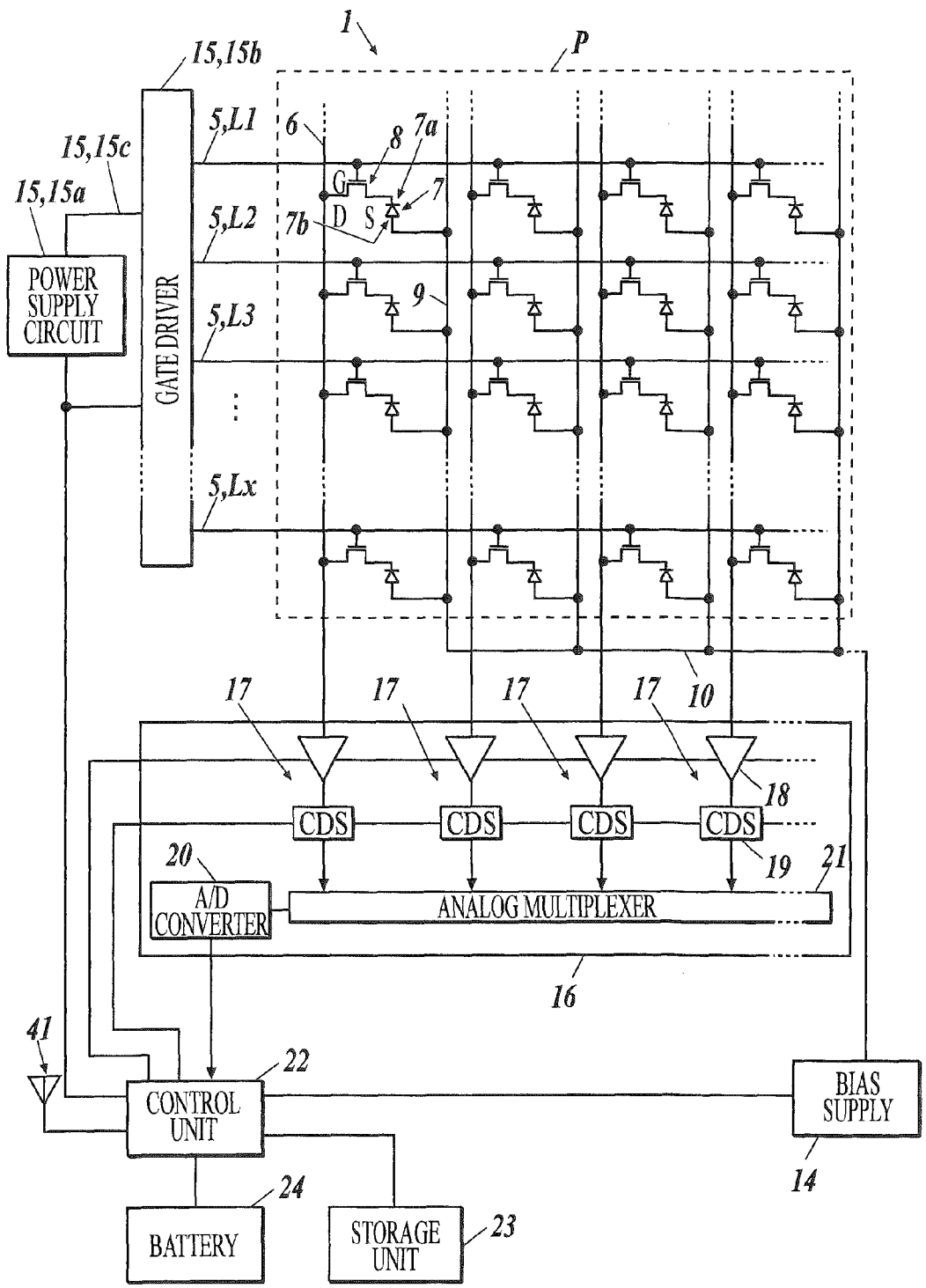
FIG. 3 is a block diagram showing an equivalent circuit of the radiation image capturing apparatus.

Next, the circuit configuration of the radiation image capturing apparatus 1 is described. FIG. 3 is a block diagram of an equivalent circuit of the radiation image capturing apparatus 1 according to the embodiments.

A first electrode 7a of each radiation detection element 7 is connected with a source electrode 8s (see "S" in FIG. 3) of a TFT 8 which is a switch element. A drain electrode 8d and a gate electrode 8g (see "D" and "G" in FIG. 3) of the TFT 8 are connected with a signal line 6 and a scan line 5, respectively.

When ON voltage is applied to the gate electrode 8g via the scan line 5 from a scan driving unit 15 described below, the TFT 8 is set to an ON state and releases electric charge accumulated in the radiation detection element 7 to the signal line 6 via the source electrode 8s and the drain electrode 8d. When OFF voltage is applied to the gate electrode 8g via the scan line 5, the TFT 8 is set to an OFF state and stops releasing electric charge from the radiation detection element 7 to the signal line 6 so that electric charge is accumulated in the radiation detection element 7.

In the embodiments, as shown in FIG. 2 or 3, a bias line 9 is provided for each column of the radiation detection elements 7 on the circuit board 4. A second electrode 7b of each of the radiation detection elements 7 is connected to the bias line 9. The bias lines 9 are bound to a tie line 10 outside the detection unit P of the circuit board 4.

The tie line 10 is connected to a bias supply 14 (see FIG. 3) via an input-output terminal 11 (also referred to as a pad, see FIG. 2). Reverse bias voltage is applied to the second electrodes 7b of the radiation detection elements 7 from the bias supply 14 via the tie line 10 and the bias lines 9.

The scan lines 5 are connected to the gate driver 15b of the scan driving unit 15 via their respective input-output terminals 11. In the scan driving unit 15, ON voltage and OFF voltage are supplied to the gate driver 15b from a power supply circuit 15a via wiring 15c, and the voltage applied to the lines L1 to Lx of the scan lines 5 can be switched between ON voltage and OFF voltage by the gate driver 15b.

Figure 6:
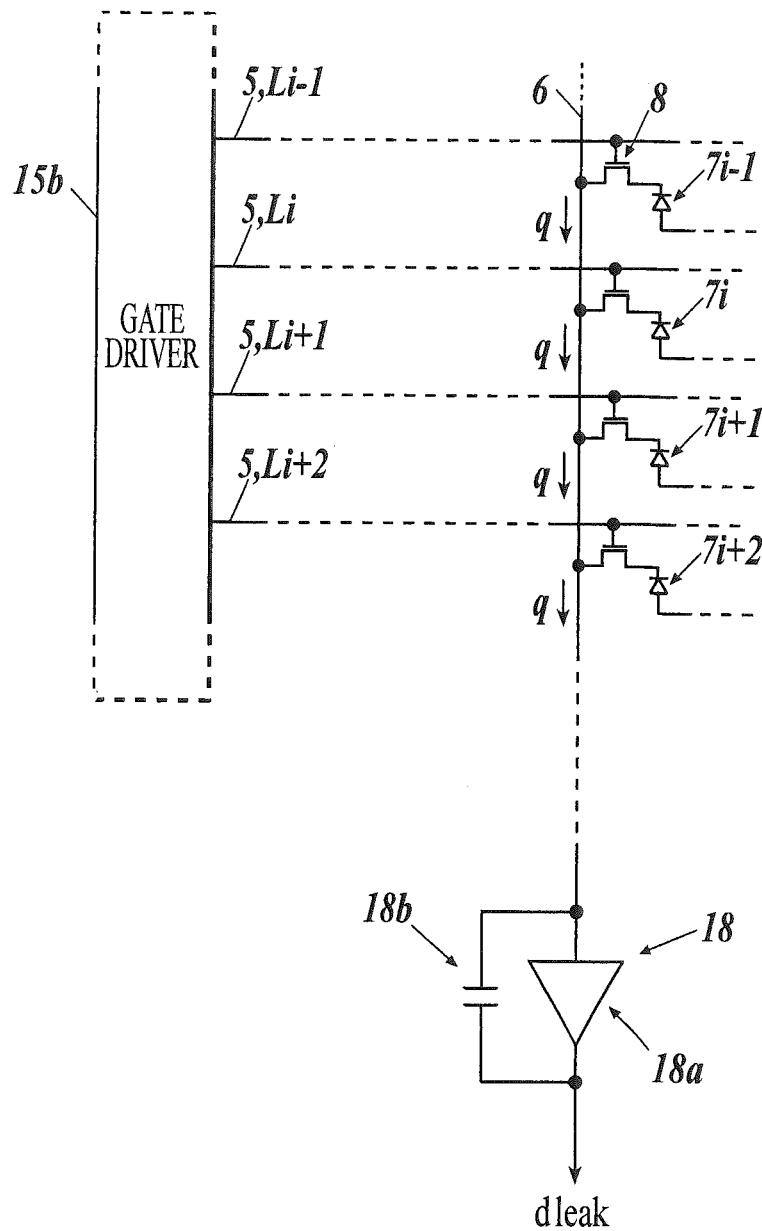
FIG. 6 illustrates that electric charges leaking from radiation detection elements via TFTs are read out as leak data.

The signal lines 6 are each connected to one of the readout circuits 17 built in each readout IC 16 via their respective input-output terminals 11. In the embodiments, each readout circuit 17 is mainly constituted of an amplifier circuit 18 and a correlated double sampling circuit 19. In addition, in the embodiments, as shown in FIG. 6 described below, the amplifier circuit 18 is constituted of a charge amplifier circuit in which, for example, an operational amplifier 18a and a capacitor 18b are connected in parallel, and a voltage value corresponding to the amount of electric charge accumulated in the capacitor 18b is output from the output side of the operational amplifier 18a.

As shown in FIG. 3, an analog multiplexer 21 and an A/D converter 20 are also included in the readout IC 16. In FIG. 3, the correlated double sampling circuit 19 is denoted as "CDS".

In the image data D readout process to read out the image data D from the radiation detection elements 7, when ON voltage is applied to a scan line 5 from the gate driver 15b of the scan driving unit 15 to set the TFTs 8 to the ON state, electric charge is released to the signal lines 6 from the radiation detection elements 7 via the TFTs 8. Then, as described above, in the amplifier circuit 18 of each readout circuit 17, a voltage value corresponding to the amount of electric charge flowing into the capacitor 18b (see FIG. 6 described below) from the radiation detection element 7 is output to the correlated double sampling circuit 19 (see FIG. 3) from the operational amplifier 18a.

The correlated double sampling circuit 19 outputs to the downstream an increment between values output from the amplifier circuit 18 before and after electric charge flows therein from the radiation detection element 7 as analog value image data D. The output image data D from the correlated double sampling circuits 19 are sequentially sent to the A/D converter 20 via the analog multiplexer 21. The received image data D are sequentially converted into digital value image data D by the A/D converter 20 and output to a storage unit 23 so as to be sequentially stored therein. The image data D readout process is thus performed.

A control unit 22 is constituted of, for example, a computer or an FPGA (Field Programmable Gate Array). The computer includes a CPU (Central Processing Unit), a ROM (Read Only Memory), a RAM (Random Access Memory) and an input-output interface which are connected to a bus (all not shown). The control unit 22 may be constituted of a specialized control circuit.

The control unit 22 controls the operation and the like of functional parts of the radiation image capturing apparatus 1. For example, the control unit 22 controls the scan driving unit 15 and the readout circuits 17 so as to perform the above-described image data D readout process.

Further, as shown in FIG. 3, the control unit 22 is connected with the storage unit 23 constituted of, for example, an SRAM (Static RAM) or an SDRAM (Synchronous DRAM). In addition, in the embodiments, the control unit 22 is connected with the aforementioned antenna device 41 and the battery 24 which supplies required power to the functional parts such as the scan driving unit 15, the readout circuits 17, the storage unit 23 and the bias supply 14.

The processes performed by the radiation image capturing apparatus 1 in radiation image capturing and the like are described after the configuration and the like of a radiation image capturing system 50 according to the embodiments are described.

[Radiation Image Capturing System]

Figure 4:
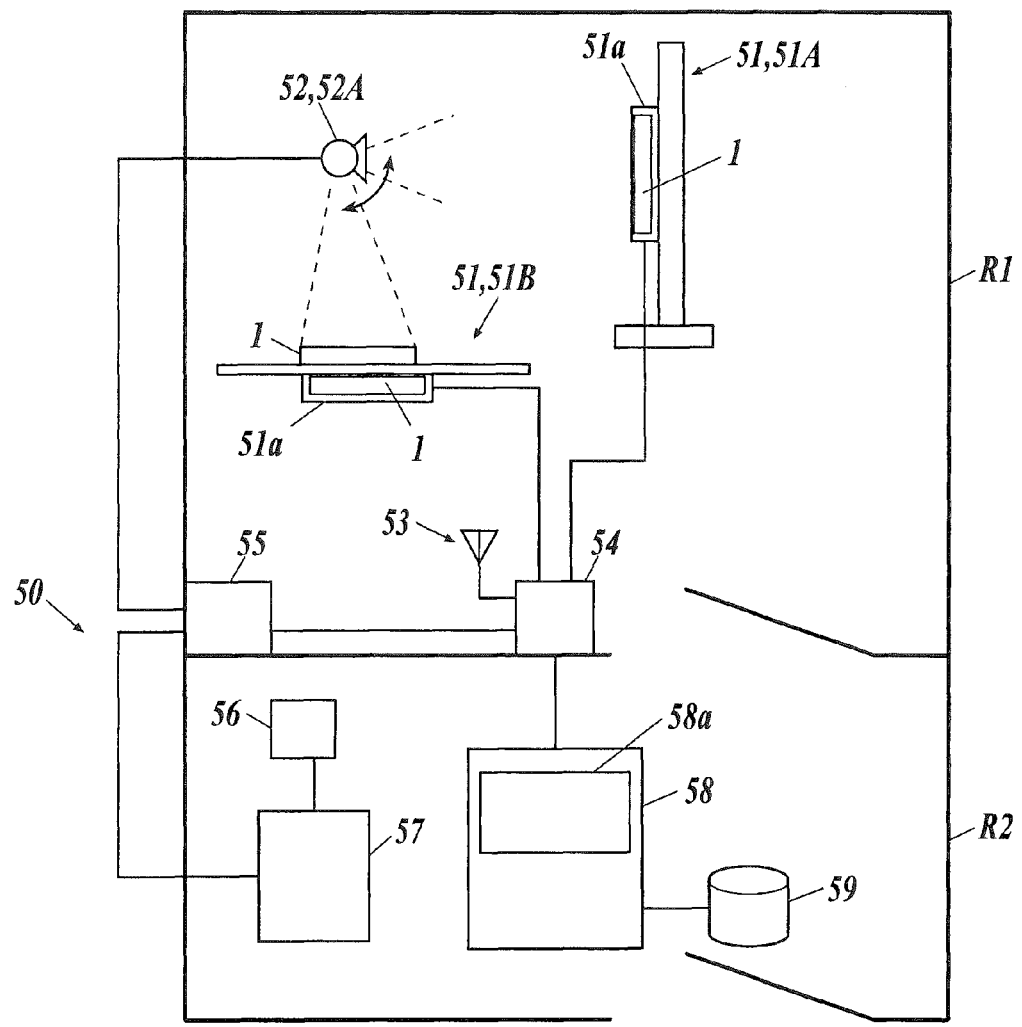

Next, the configuration and the like of the radiation image capturing system 50 according to the embodiments are described. FIG. 4 shows a configuration example of the radiation image capturing system 50 according to the embodiments. In FIG. 4, the radiation image capturing system 50 is built in a radiography room R1 and the like.

Bucky devices 51 are disposed in the radiography room R1. Each of the Bucky devices 51 can hold the radiation image capturing apparatus 1 by a cassette holder 51a. Although a standing X-ray Bucky device 51A and a supine X-ray Bucky device 51B are provided as the Bucky devices 51 in FIG. 4, for example, only one of the Bucky devices 51 may be provided.

As shown in FIG. 4, the radiography room R1 is provided with at least one radiation source 52A for the radiation generation apparatus 55 to emit radiation to the radiation image capturing apparatus 1 set on the Bucky device 51 to irradiate the radiation image capturing apparatus 1 through a subject. In the embodiments, both the standing X-ray Bucky device 51A and the supine X-ray Bucky device 51B can be irradiated by the radiation source 52A by moving the radiation source 52A or changing the direction of the radiation.

The radiography room R1 is provided with a relay 54 (also referred to as a base station or the like) to relay communication and the like between apparatuses and the like disposed inside and outside the radiography room R1. In the embodiments, the relay 54 is provided with an access point 53 so that the radiation image capturing apparatus 1 can send and receive the image data D, signals and the like to/from another apparatus or the like by wireless transmission.

In addition, the relay 54 is connected with the radiation generation apparatus 55 and the console 58. In the relay 54, a not-shown converter is built which converts LAN (Local Area Network) signals or the like sent from, for example, the radiation image capturing apparatus 1 or the console 58 to the radiation generation apparatus 55 into signals or the like for the radiation generation apparatus 55 and vice versa.

In a front room R2 (also referred to as an operation room or the like) of the embodiments, an operator console 57 for the radiation generation apparatus 55 is disposed. The operator console 57 has an exposure switch 56 which is operated by an operator to command the radiation generation apparatus 55 to start irradiation, for example. When the exposure switch 56 is operated by an operator, the radiation generation apparatus 55 emits radiation from the radiation source 52.

In addition, the radiation generation apparatus 55 performs various types of control. For example, the radiation generation apparatus 55 controls the radiation source 52 to emit radiation of an appropriate radiation dose or at an appropriate dose rate (i.e. radiation dose per unit time) by supplying, on the basis of a radiography condition such as a tube voltage set by the console 58, the set tube voltage to the radiation source 52, for example.

As shown in FIG. 4, the console 58 constituted of a computer or the like is disposed in the front room R2 in the embodiments. The console 58 can be disposed at any appropriate place, for example, in the radiography room R1, outside the front room R2 or in another room.

The console 58 includes: a display unit 58a which includes a CRT (Cathode Ray Tube), an LCD (Liquid Crystal Display) or the like; and a not-shown input unit such as a mouse or a keyboard. In the embodiments, as described below, the radiography condition such as a tube voltage V to be set to the radiation generation apparatus 55 can be set on the console 58 with the input unit. The console 58 is connected with or includes a storage unit 59 constituted of an HDD (Hard Disk Drive) or the like.

Figure 5:
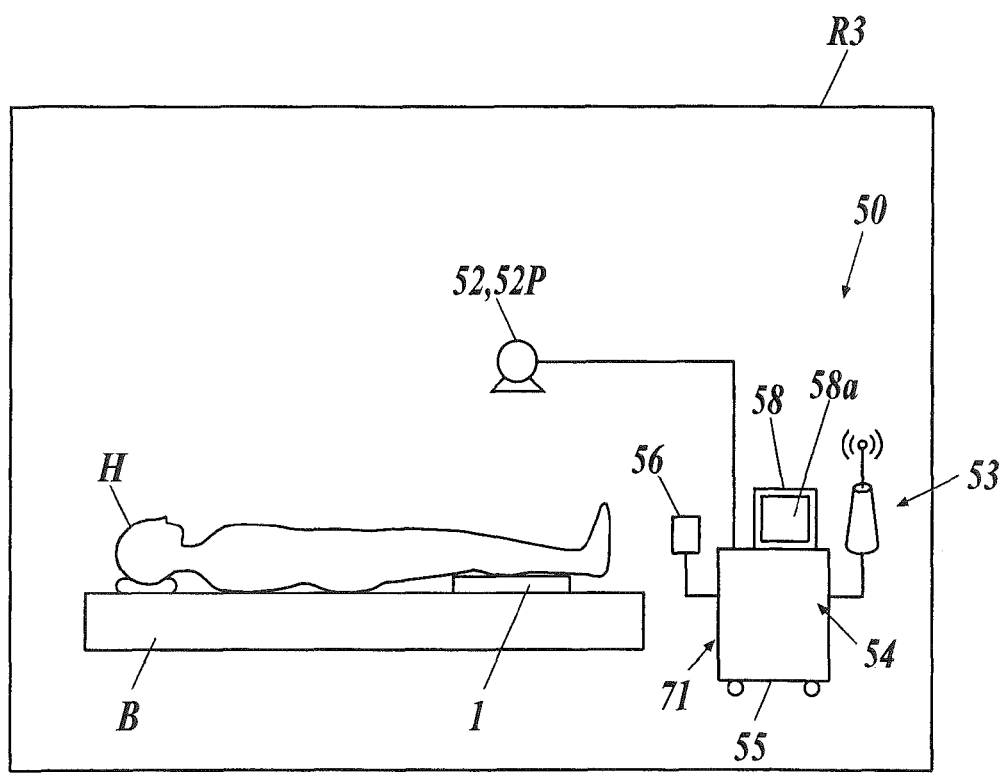

As shown in FIG. 5, the radiation image capturing apparatus 1 can also be used alone without being set on the Bucky device 51.

For example, if a patient H cannot stand up from a bed B in a patient's room R3 and accordingly cannot go to the radiography room R1 or if the radiation image capturing system 50 including the radiation image capturing apparatus 1 is taken to a home of a home-care patient to perform radiation image capturing therein, as shown in FIG. 5, which shows the patient H in the patient's room R3, the radiation image capturing apparatus 1 can be taken to the patient's room R3 or the like and inserted between the bed B and the patient's body or placed on the patient's body.

When the radiation image capturing apparatus 1 is used in the patient's room R3 or the like, instead of the radiation generation apparatus 55 fixed to the radiography room R1, as shown in FIG. 5, a portable radiation generation apparatus 55 is taken to the patient's room R3 by, for example, mounting the portable radiation generation apparatus 55 on a nursing cart 71.

A radiation source 52P for the portable radiation generation apparatus 55 can emit radiation in a desired direction. Thus, the radiation source 52P, i.e. the portable radiation generation apparatus 55, can irradiate from an appropriate distance and an appropriate direction the radiation image capturing apparatus 1 inserted between the bed B and the patient's body or placed on the patient's body.

The portable radiation generation apparatus 55 is provided with a built-in relay 54 having an access point 53. As with the fixed radiation generation apparatus 55, the relay 54 relays, for example, communication between the portable radiation generation apparatus 55 and the console 58 and communication and transmission of the image data D between the radiation image capturing apparatus 1 and the console 58.

As shown in FIG. 4, the radiation image capturing apparatus 1 can also be inserted between the body of a not-shown patient laying on the supine X-ray Bucky device 51B in the radiography room R1 and the supine X-ray Bucky device 51B, or be placed on the patient's body on the supine X-ray Bucky device 51B. In these cases, either the portable radiation generation apparatus 55 or the fixed radiation generation apparatus 55 in the radiography room R1 can be used.

In the embodiments, as described above, the console 58 sends signals and the like to the radiation image capturing apparatus 1 and the (fixed or portable) radiation generation apparatus 55 to control them. The console 58 also functions as an image processing apparatus. When receiving the image data D and the like sent from the radiation image capturing apparatus 1, on the basis of the image data D and the like, the console 58 performs accurate image processing such as gain control, defective pixel correction or gradation processing suitable for a radiography part of the body of a subject (i.e. a patient) to create a radiation image p.

[Irradiation Start Detection Process by Radiation Image Capturing Apparatus]

An irradiation start detection process performed by the radiation image capturing apparatus 1 used in the radiation image capturing system 50 is described. As described above, the inventors of the present invention et al. have found several methods by which the radiation image capturing apparatus itself detects start of irradiation thereof (i.e. start of being irradiated). In the following, these methods are described.

[Detection Method 1]

The radiation image capturing apparatus 1 can be configured to repeatedly perform a leak data dleak readout process by making the readout circuits 17 perform readout operations in a state in which OFF voltage is applied to the scan lines 5 from the gate driver 15b (see FIG. 3) since before the radiation image capturing apparatus 1 is irradiated. The detection method 1 is detailed in International Publication No. WO 2011/135917, which was filed by the applicant of the present application. Hence, for detail, this patent document should be referred to.

When the TFTs 8 are in the OFF state by OFF voltage being applied to the scan lines 5 from the gate driver 15b, as shown in FIG. 6, electric charges q leaking from the radiation detection elements 7 via the TFTs 8 in the OFF state are accumulated in the capacitors 18b of the amplifier circuits 18. That is, in the capacitor 18b of each amplifier circuit 18, the sum of the electric charges q leaking from the radiation detection elements 7 via the TFTs 8 are accumulated.

When each readout circuit 17 performs the readout operation in this state, from the output side of the operational amplifier 18a of the amplifier circuit 18, a voltage value corresponding to the sum of the electric charges q leaking from the radiation detection elements 7 via the TFTs 8 is output. Consequently, data corresponding to the sum of the electric charges q leaking from the radiation detection elements 7 via the TFTs 8 is read out. The data read out in this way is leak data dleak.

With this configuration, when irradiation of the radiation image capturing apparatus 1 starts, the electric charges q leaking from the radiation detection elements 7 via the TFTs 8 to the signal lines 6 increase. Hence, at the time (time t1 in FIG. 7, for example) when irradiation of the radiation image capturing apparatus 1 starts, the value of the leak data dleak read out rapidly increases.

Figure 7:
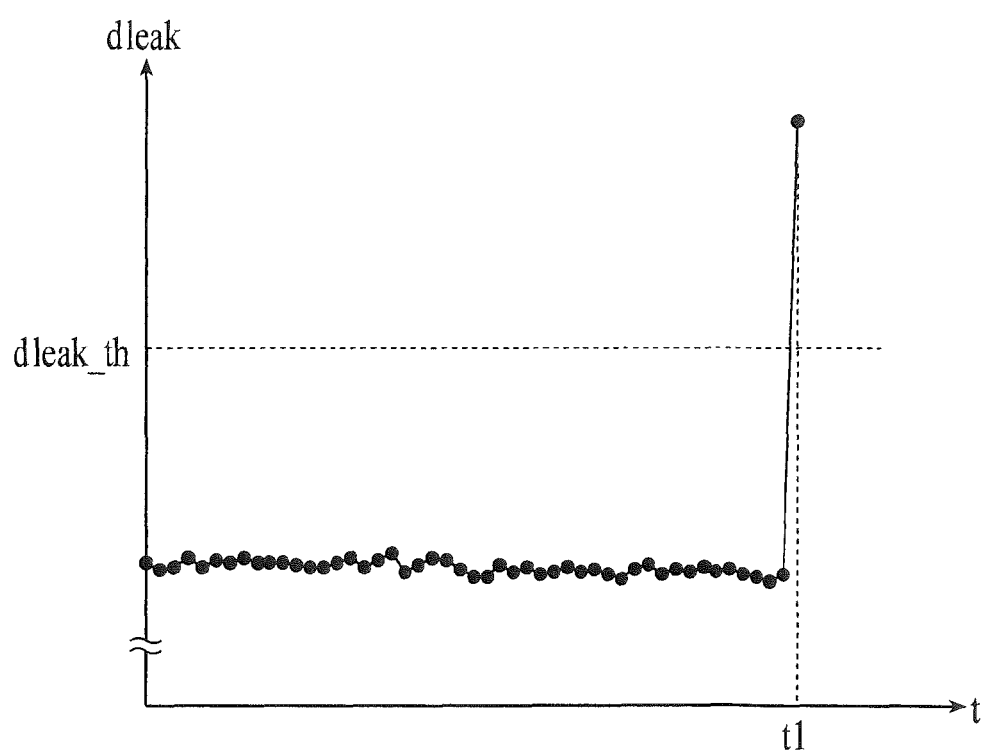
FIG. 7 is a graph showing an example of change of the leak data read out over time.

Then, by using the fact that the value of the leak data dleak increases, as shown in FIG. 7, the radiation image capturing apparatus 1 can be configured to detect that the read-out leak data dleak is equal to or more than a preset threshold dleak-th, thereby detecting start of irradiation thereof.

When the radiation image capturing apparatus 1 is configured to use the leak data dleak to detect start of irradiation thereof, and OFF voltage is continuously applied to the scan lines 5 from the gate driver 15b, the TFTs 8 are set to the OFF state and remain in the OFF state. Then, dark electric charges are continuously accumulated in the radiation detection elements 7.

Figure 8:
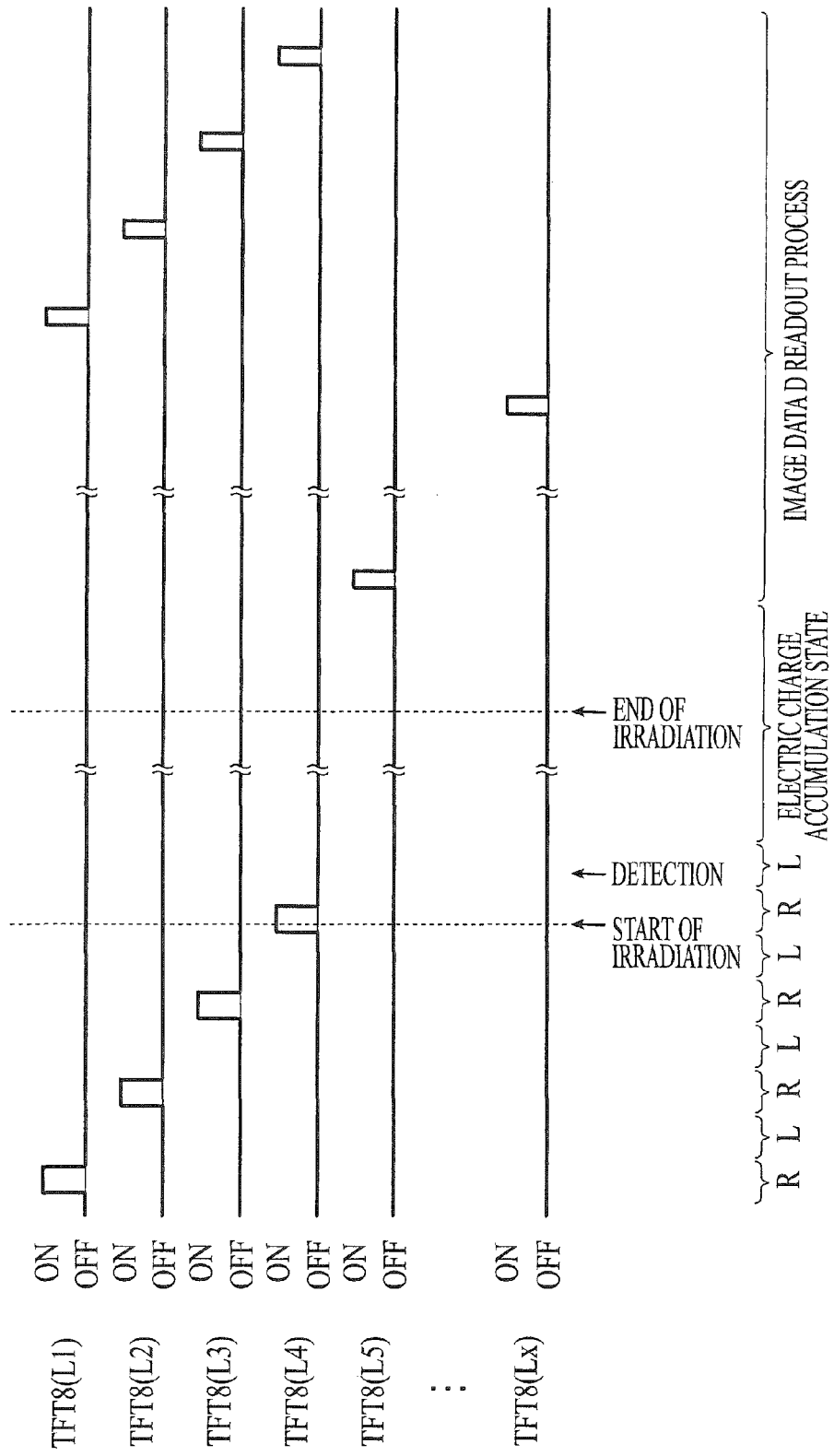
FIG. 8 is a timing chart for explaining, for example, the timing at which the ON voltage is applied to scan lines in a case where start of irradiation is detected on the basis of the leak data.

Hence, as shown on the left side in FIG. 8, it is preferable that the radiation image capturing apparatus 1 be configured to alternately perform the leak data dleak readout process ("L" in FIG. 8) to read out the leak data dleak and a radiation detection element 7 reset process ("R" in FIG. 8) to reset the radiation detection elements 7.

The radiation detection element 7 reset process may be performed by sequentially applying ON voltage to the lines L1 to Lx of the scan lines 5 from the gate driver 15b (see FIG. 3) of the scan driving unit 15 as shown in FIG. 8 or by applying ON voltage to the lines L1 to Lx of the scan lines 5 from the gate driver 15b thereof at once although not shown.

[Detection Method 2]

Instead of performing the leak data dleak readout process since before the radiation image capturing apparatus 1 is irradiated as described above, the radiation image capturing apparatus 1 can be configured to repeatedly perform an image data readout process to read out image data by driving, for example, the scan driving unit 15 and the readout circuits 17 (see FIG. 3).

The detection method 2 is detailed in the above-mentioned International Publication No. WO 2011/152093, which was filed by the applicant of the present application. Hence, for detail, this patent document should be referred to. In the following, the image data read out before start of irradiation of the radiation image capturing apparatus 1 is referred to as data d for irradiation start detection to be distinguished from image data D which is read out for the so-called actual image.

With this configuration, before irradiation of the radiation image capturing apparatus 1 starts, the so-called dark image data (data d for irradiation start detection), which is read out with no irradiation, is read out. When irradiation of the radiation image capturing apparatus 1 starts, electric charges are generated in the radiation detection elements 7 by the irradiation, and the electric charges are read out as the data d for irradiation start detection.

Hence, as with the leak data dleak (see FIG. 7), at the time when irradiation of the radiation image capturing apparatus 1 starts, the value of the data d for irradiation start detection rapidly increases. Then, the radiation image capturing apparatus 1 can be configured to detect that the read-out data d for irradiation start detection is equal to or more than a preset threshold dth, thereby detecting start of irradiation thereof.

[Process after Detection of Start of Irradiation]

In either of the detection methods 1 and 2, as shown in FIG. 8, which shows the case of the detection method 1, when detecting start of irradiation of the radiation image capturing apparatus 1 ("Detection" in FIG. 8), the control unit 22 of the radiation image capturing apparatus 1 applies OFF voltage to the lines L1 to Lx of the scan lines 5 from the gate driver 15*b*.

Thus, all the TFTs 8 are set to the OFF state, and the radiation image capturing apparatus 1 moves to the electric charge accumulation state in which the electric charges generated in the radiation detection elements 7 by irradiation are accumulated therein. Then, for example, when a predetermined time elapses after the radiation image capturing apparatus 1 moves to the electric charge accumulation state, the image data D readout process to read out the image data D for the actual image starts.

In the embodiments, as shown in FIG. 8, the image data D readout process is performed by sequentially applying ON voltage from the gate driver 15*b* to the scan lines 5 starting from the scan line 5 to which ON voltage has been scheduled to be applied (in the case of FIG. 8, the line L5 of the scan lines 5) next to the scan line 5 to which ON voltage has been applied last before detection of start of the irradiation (in the case of FIG. 8, the line L4 of the scan lines 5).

However, this is not a limitation but an example. Hence, although not shown, the image data D readout process may be performed by sequentially applying ON voltage to the lines L1 to Lx of the scan lines 5 starting from the first line L1 of the scan lines 5.

[Modified Irradiation Start Detection Method]

The above-described detection methods 1 and 2 can be modified described below. In the embodiments, the modified detection methods described below are actually used to detect start of irradiation of the radiation image capturing apparatus 1.

In the following, a detection method modified from the detection method 1, by which before radiation image capturing, the leak data dleak readout process and the radiation detection element 7 reset process are alternately performed and start of irradiation is detected on the basis of the read-out leak data dleak, is mainly described. The same applies to the detection method 2. These modified detection methods are detailed, for example, in Japanese Patent Application Laid-Open Publication No. 2012-176155, which was filed by the applicant of the present application. Hence, for detail, this patent document should be referred to.

In the case where the detection method 1 is adopted, the number of leak data dleak read out by performing the leak data dleak readout process one time is several thousands to several tens of thousands because the detection unit P (see FIG. 2 or 3) of the radiation image capturing apparatus 1 usually has several thousands to several tens of thousands of scan lines 5 arranged, and the scan lines 5 are provided with the readout circuits 17 one-to-one.

If determination whether or not the leak data dleak is equal to or more than the threshold dleak-th is made on all the leak data dleak each time the leak data dleak readout process is performed, the load of the irradiation start detection process is very heavy. Consequently, there is a risk of not detecting start of the irradiation on a real-time basis.

Hence, in the embodiments, as described below, the number of data to be subjected to the determination is reduced for the irradiation start detection process.

In the embodiments, for example, 128 or 256 readout circuits 17 are built in each readout IC 16 (see FIG. 3). That is, the signal lines 6 are connected to 128 or 256 readout circuits 17 in one readout IC 16 one-to-one, and 128 or 256 leak data dleak are read out from each readout IC 16 each time the leak data dleak readout process is performed.

Then, for example, the average, the sum, the median, the maximum value or the like ("statistic" hereinafter) of, for example, 256 leak data dleak, which are output from each readout IC 16, is calculated each time the leak data dleak readout process is performed. Then, with respect to each readout IC 16, whether or not the calculated statistic dleak_st(z) of the leak data dleak of the readout IC 16 is equal to or more than a threshold dthA set for the statistic dleak_st(z) is determined. The "z" represents the number of a readout IC 16.

If, for example, the detection unit P has 4,096 signal lines 6 arranged, and 128 readout circuits 17 are built in one readout IC 16 (i.e. 128 signal lines 6 are connected to one readout IC 16), the number of readout ICs 16 is "4,096/128=32".

With the above-described configuration, instead of 4,096 leak data dleak on which the determination whether or not the leak data dleak is equal to or more than the threshold dleak th needs to be made, the determination needs to be made only on 32 statistics dleak_st(z) (z=1 to 32). Accordingly, the load of the irradiation start detection process can be reduced.

[Detection Method A (Calculus of Finite Differences)]

In order to further reduce the load of the above-described determination process in the irradiation start detection process, the control unit 22 can be configured to extract the maximum value of the 32 statistics dleak_st(z) calculated from the leak data dleak output from the readout ICs 16 by the leak data dleak readout process performed one time and determine whether or not the maximum value is equal to or more than a threshold.

With this configuration, on the only one statistic, namely, the maximum value extracted from the 32 statistics dleak_st(z), the determination whether or not the statistic (maximum value) is equal to or more than a threshold needs to be made. Accordingly, the load of the irradiation start detection process can be very light.

However, usually, the readout characteristic varies among the readout ICs 16. Hence, even when the sums of the electric charges q (see FIG. 6) leaking from the radiation detection elements 7 to the respective signal lines 6 are the same, the statistics dleak_st(z) of some readout ICs 16 may be always more than those of other readout ICs 16 or vice versa.

Figure 9:
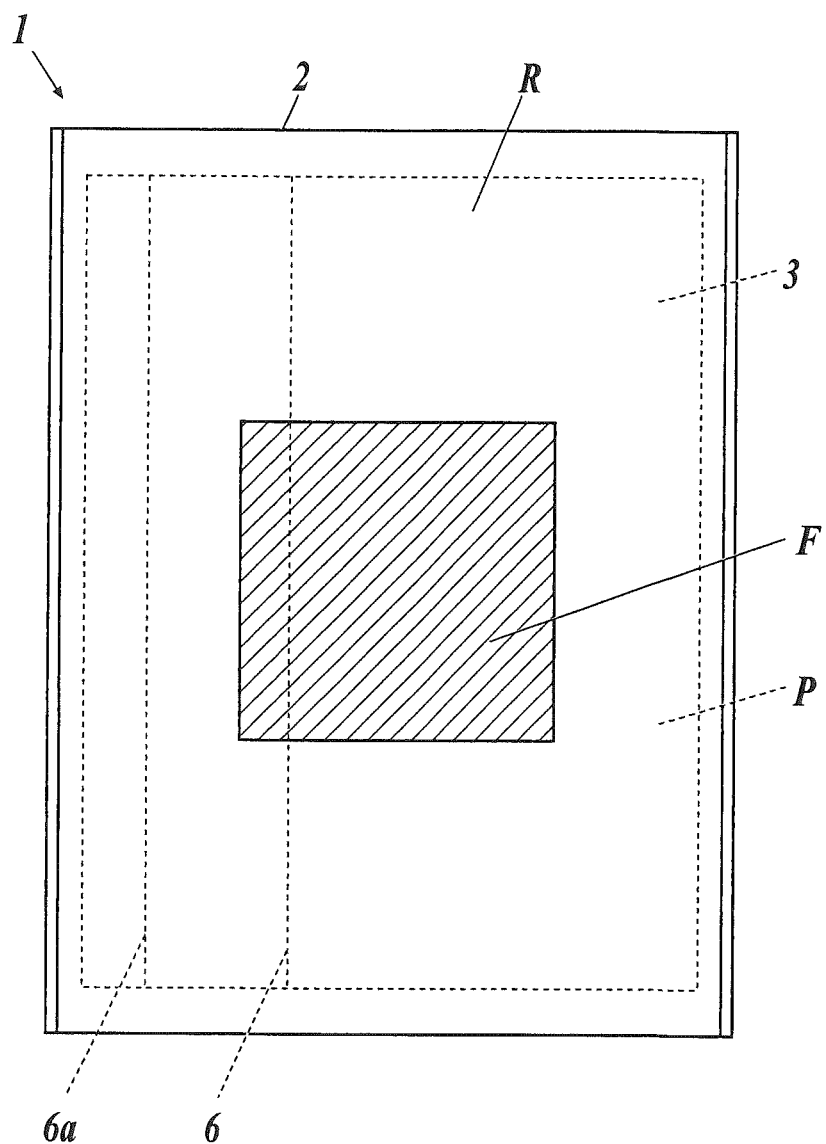
FIG. 9 shows the radiation image capturing apparatus, the irradiation field of which is limited.

Then, consideration is given to a case where in such a circumstance, the radiation image capturing apparatus 1 is irradiated having the irradiation field F limited to the center part of the detection unit P as shown in FIG. 9. If a signal line(s) 6*a* connected to a readout IC 16 (16δ) the statistic dleak_st(z) of which is always more than that of each of the other readout ICs 16 exists outside the irradiation field F, as shown in FIG. 10, even when the statistic dleak_st(z) (see "γ" in FIG. 10) of the leak data dleak output from a readout IC 16γ to which signal lines 6 existing inside the irradiation field F are connected increases by irradiation, the statistic dleak_st(z) of the leak data dleak output from the readout IC 16γ may not be equal to or more than that (see "δ" in FIG. 10) of the leak data dleak output from the readout IC 16δ.

Figure 10:
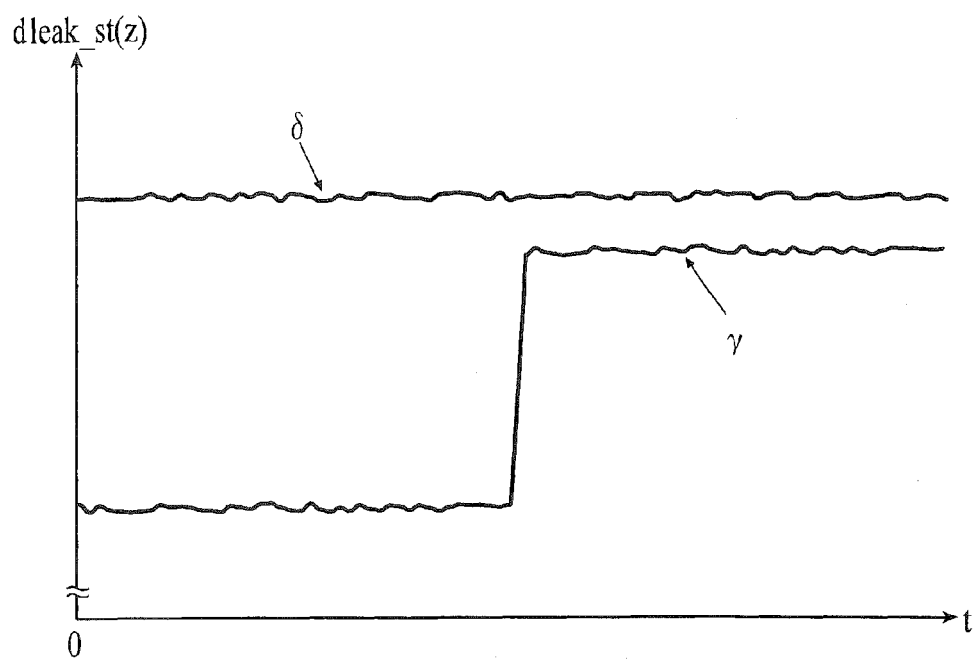
FIG. 10 is a graph showing an example of change of the average (statistic) of the leak data read out by readout circuits of each readout IC over time.

If the maximum value is extracted from the statistics dleak_st(z) of the leak data dleak output from the readout ICs 16 in this case, the statistic dleak_st(z) indicated by δ in FIG. 10 is extracted. However, this extracted statistic dleak_st(z) does not change by irradiation and hence does not become equal to or more than the threshold. Accordingly, the irradiation cannot be detected.

In order to prevent such a problem from arising, for example, the below-described method using a moving average can be adopted.

Figure 11:
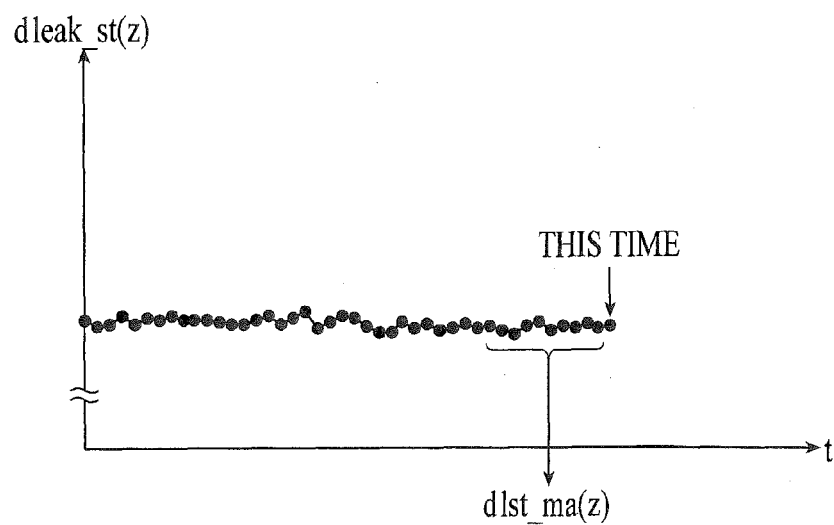
FIG. 11 is a graph for explaining a calculation method of a moving average.

That is, each time the leak data dleak readout process is performed, for each readout IC 16, the moving average dlst_ma(z) is calculated on the basis of the statistics dleak_st(z) of the leak data dleak output from the readout IC 16. More specifically, each time the leak data dleak readout process is performed, the statistic dleak_st(z) of the leak data dleak output from each readout IC 16 is calculated, and also, as shown in FIG. 11, the average (i.e. the moving average dlst_ma(z)) of the statistics dleak_st(z) of the leak data dleak output from the same readout IC 16 calculated at the last predetermined times (ten times, for example) of the leak data dleak readout process including the most recent time before this time is calculated.

As a calculation method of the moving average dlst_ma(z), a known method such as the simple moving average, weighted moving average or exponential moving average can be used.

For each readout IC 16, the difference Δd(z) between the statistic dleak_st(z) calculated at this time's leak data dleak readout process and the moving average dlst_ma(z) is calculated by the following equation (1).

$$\Delta d(z) = d\text{leak\_st}(z) - d\text{lst\_ma}(z) \quad (1)$$

Thus, for each readout IC 16, the control unit 22 calculates the statistic dleak_st(z) of the leak data dleak output from the readout IC 16 by the leak data dleak readout process performed one time and also calculates the difference Δd(z) between the statistic dleak_st(z) and the moving average dlst_ma(z).

Then, the control unit 22 extracts the maximum value Δdmax from the calculated differences Δd(z) (32 differences Δd(z) in this case) and determines whether or not the maximum value Δdmax is equal to or more than a threshold Δdth. Hereinafter, the irradiation start detection method based on this detection method A is referred to as calculus of finite differences.

With this configuration, although the readout characteristic varies among the readout ICs 16, the variation can be removed because, for each readout IC 16, the difference Δd(z) between the statistic dleak_st(z) and the moving average dlst_ma(z) is calculated from the leak data dleak read out by the same readout IC 16, namely, read out under the same readout characteristic.

Figure 12:
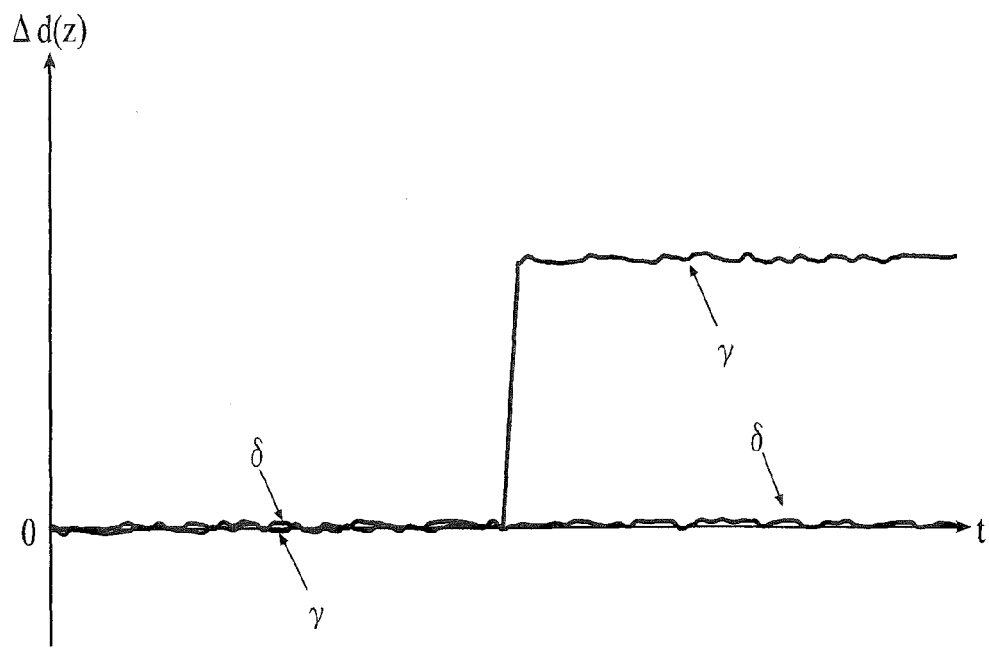
FIG. 12 is a graph showing an example of change of the difference between the statistic and the moving average calculated for each readout IC over time.

That is, although the readout characteristic varies among the readout ICs 16 as shown in FIG. 10, unless the radiation image capturing apparatus 1 is irradiated, the difference Δd(z) of any of the readout ICs 16 including the readout ICs 16γ and 16δ is approximately 0 as shown in FIG. 12 (see γ and δ before start of irradiation in FIG. 12).

Therefore, the difference Δd(z) of each readout IC 16 is a value which purely reflects increase or no increase of the statistic dleak_st(z) of the leak data dleak output from the readout IC 16 from the previous data. Accordingly, start of irradiation is detected on the basis of the values, and the problem shown in FIG. 10 can be prevented from arising for sure.

Figure 13:
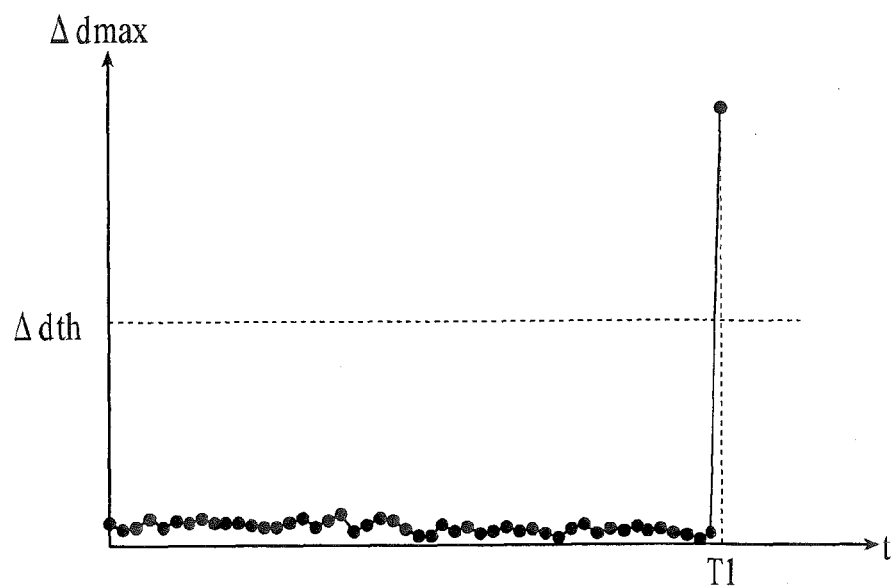
FIG. 13 is a graph showing an example of change of the maximum value of the differences over time.

When irradiation of the radiation image capturing apparatus 1 starts (see a time T1 in FIG. 13), in at least one of the readout ICs 16, the statistic dleak_st(z) of the leak data dleak read out at this time's leak data dleak readout process is significantly larger than the moving average dlst_ma(z), and accordingly, as shown in FIG. 13, the maximum value Δdmax is equal to or more than the threshold Δdth for sure. Accordingly, start of irradiation of the radiation image capturing apparatus 1 can be accurately detected.

As described above, in the embodiments, in the case where the moving average dlst_ma(z) is calculated, as shown in FIG. 11, the moving average dlst_ma(z) is calculated for each readout IC 16 from the statistics dleak_st(z) calculated at the last predetermined times (ten times, for example) of the leak data dleak readout process including the most recent time before this time.

Figure 14:
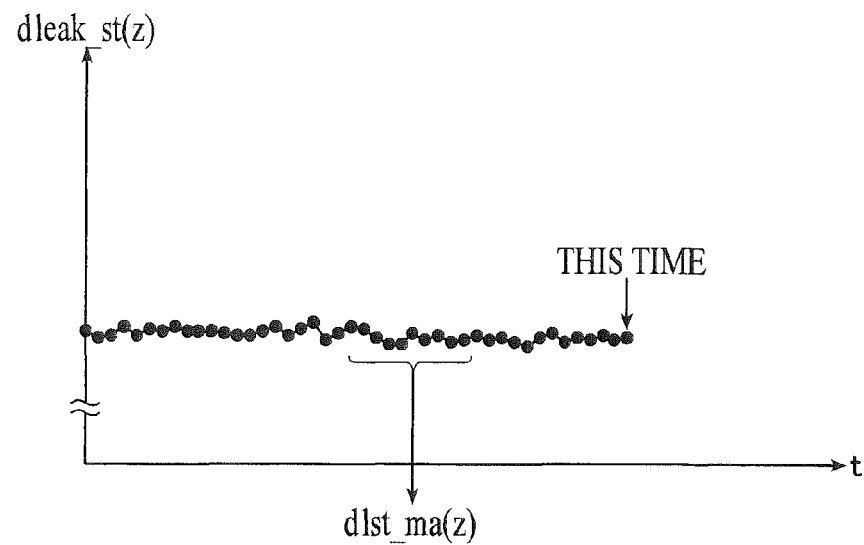
FIG. 14 is a graph for explaining a calculation method of the moving average different from the calculation method shown in FIG. 11.

However, instead of this configuration, as shown in FIG. 14, the moving average dlst_ma(z) may be calculated for each readout IC 16 from the statistics dleak_st(z) calculated at predetermined times (ten times, for example) of the leak data dleak readout process in the past, going back from a time which is predetermined times (10 or 50 times, for example) before this time.

With this configuration, the following advantageous effects can be obtained when, for example, a radiation generation apparatus 55 emits very weak radiation (i.e. radiation at a very low dose rate) to the radiation image capturing apparatus 1 and the statistic dleak_st(z) increases gradually (i.e. little by little).

That is, in the case of FIG. 11, with the configuration shown in FIG. 11, the difference Δd(z) between the statistic dleak_st(z) and the moving average dlst_ma(z) cannot be large and the S/N ratio of the difference Δd(z) is not always good, but with the configuration shown in FIG. 14, the difference Δd(z) therebetween can be relatively large and the S/N ratio of the difference Δd(z) can be improved.

As described above, for example, in the case where a radiation generation apparatus 55 emits very weak radiation to the radiation image capturing apparatus 1, the accuracy of the irradiation start detection process using the calculus of finite differences (detection method A) can be improved.

[Detection Method B (Integration)]

When a dose rate at which a radiation generation apparatus 55 emits radiation to the radiation image capturing apparatus 1 is very low, the statistic dleak_st(z), such as the average, of the leak data dleak of each readout IC 16 calculated as described above is small. Hence, the statistic dleak_st(z) may not be equal to or more than the threshold dthA even when the radiation image capturing apparatus 1 is irradiated.

Similarly, in the case where the calculus of finite differences (detection method A) is adopted, the difference Δd(z) between the statistic dleak_st(z) and the moving average dlst_ma(z) when the radiation image capturing apparatus 1 is irradiated may be small. Hence, the difference Δd(z) may not be equal to or more than the threshold Δdth even when the radiation image capturing apparatus 1 is irradiated.

It means that even with calculus of finite differences (detection method A), the radiation image capturing apparatus 1 may not detect start of irradiation although the radiation image capturing apparatus 1 is irradiated.

Then, for example, for each readout IC 16, the integrated value ΣΔd of the differences Δd(z) over time each between the statistic dleak_st(z) and the moving average dlst_ma(z) is calculated. Then, whether or not a readout IC 16 having an integrated value $\Sigma\Delta d$ being equal to or more than a threshold $\tau\Delta dth$ exists is determined. Hereinafter, the start detection method based on this detection method B is referred to as integration.

With this configuration, although not shown, before the radiation image capturing apparatus 1 is irradiated, the statistic dleak_st(z) of the leak data dleak fluctuates and is larger at one point of time but smaller at another point of time than the moving average dlst_ma(z). Consequently, the integrated value $\tau\Delta d$ of the differences $\Delta d(z)$ hovers around 0.

When irradiation of the radiation image capturing apparatus 1 starts, the statistic dleak_st(z) is significantly larger than the moving average dlst_ma(z). Consequently, the difference $\Delta d(z)$ therebetween is often a positive value. That is, with the above-described configuration, when irradiation of the radiation image capturing apparatus 1 starts, the integrated value $\Sigma\Delta d$ of the differences $\Delta d(z)$ increases to be larger than the threshold $\Sigma\Delta dth$.

Accordingly, even when the dose rate at which a radiation generation apparatus 55 emits radiation to the radiation image capturing apparatus 1 is very low, start of irradiation of the radiation image capturing apparatus 1 can be accurately detected.

In the integration (detection method B), when the differences $\Delta d(z)$ are integrated unlimitedly, the integrated value $\Sigma\Delta d$ of the differences $\Delta d(z)$ is equal to or more than the threshold $\Sigma\Delta dth$ although the radiation image capturing apparatus 1 is not irradiated. Consequently, start of irradiation of the radiation image capturing apparatus 1 may be falsely detected.

Hence, in the case where the detection method B (integration) is adopted, it is preferable that the number of times or the time (time length/period) that the differences $\Delta d(z)$ are integrated be limited. That is, it is preferable to decide that, for example, up to how many times of the leak data dleak readout process in the past including this time (integration number) or up to how many seconds during which the leak data dleak is repeatedly performed in the past including the current second at which this time's leak data dleak readout process is performed (integration time), the calculated differences $\Delta d(z)$ are integrated.

The leak data dleak readout process is performed at intervals of a predetermined time. Hence, presetting the integration number and presetting the integration time are the same thing in the end.

[Irradiation Start Detection Process of Embodiments]

In the radiation image capturing apparatus 1 of the embodiments, the control unit 22 thereof detects start of irradiation thereof by using the two detection methods, i.e. the calculus of finite differences (detection method A) and the integration (detection method B). When start of the irradiation is detected by either of the two detection methods, the control unit 22 determines that the irradiation starts.

The irradiation start detection method used by the control unit 22 is not limited to the calculus of finite differences (detection method A) or the integration (detection method B), and hence other modified detection methods such as the Max-Min method described, for example, in the above-mentioned Japanese Patent Application Laid-Open Publication No. 2012-176155 can be adopted. The present invention is applicable to the cases where these other detection methods are used.

[Configuration and the Like Specific to the Present Invention]

Next, the configuration and the like specific to the present invention are described through several embodiments. The operation of the radiation image capturing system 50 according to each embodiment is also described.

First Embodiment

Maximum Body Thickness Up to which Start of Irradiation can be Detected

In a first embodiment of the present invention, the radiation image capturing system 50 includes a calculation unit which calculates, before radiation image capturing, the maximum body thickness BT up to which the control unit 22 of the radiation image capturing apparatus 1 itself can detect start of irradiation thereof by the radiation generation apparatus 55 through a subject. The calculation unit calculates the maximum body thickness BT for each radiation generation apparatus 55 on the basis of the leak data dleak or the data d for irradiation start detection (or the difference $\Delta d(z)$ between the statistic of the data and the moving average (calculus of finite differences) or the integrated value $\Sigma\Delta d$ of the differences $\Delta d(z)$ (integration)) read out in the radiation image capturing apparatus 1 irradiated by the radiation generation apparatus 55.

This calculation process may be performed by the console 58 (in this case, the console 58 is the calculation unit) or by a computer such as a not-shown image processing apparatus in the radiation image capturing system 50. Alternatively, a specialized computer as the calculation unit may be provided.

In the present invention, attention is paid to the maximum body thickness BTmax up to which the control unit 22 of the radiation image capturing apparatus 1 can detect start of irradiation thereof through a subject. The reasons are described below.

As described above, even when the radiation image capturing apparatus 1 is adjusted to detect radiation emitted from a radiation generation apparatus 55 to a subject (i.e. a patient or the like), the control unit 22 of the radiation image capturing apparatus 1 may not be able to detect radiation (i.e. start of irradiation) when another radiation generation apparatus 55 emits radiation to the subject.

According to the studies of the inventors of the present invention et al., it has been found that one of the causes of the above phenomenon is the (actual) body thickness BT of a subject.

The fatter a patient as a subject is, namely, the larger the body thickness BT of a subject is, the larger the proportion of radiation absorbed or scattered in the subject's body to the whole radiation emitted from a radiation generation apparatus 55 is. Hence, the fatter a subject is, the lower a dose rate at which the radiation reaches the radiation image capturing apparatus 1 is, and depending on the irradiation characteristic of the radiation generation apparatus 55 (i.e. the radiation generation apparatus 55 which emits radiation at a lower dose rate than another even when the same tube voltage V or the like is set to both), the radiation image capturing apparatus 1 cannot detect start of irradiation thereof.

The inventors of the present invention et al. have analyzed this phenomenon in detail and found that, in a case where a radiation generation apparatus 55 emits radiation to the radiation image capturing apparatus 1 at a predetermined dose rate, the body thickness BT through which the control unit 22 of the radiation image capturing apparatus 1 can detect start of irradiation thereof on the basis of the leak data dleak or the data d for irradiation start detection read out in the radiation image capturing apparatus 1 varies.

That is, the maximum value (maximum body thickness BTmax) exists in the body thickness BT, through which the control unit 22 of the radiation image capturing apparatus 1 can detect start of irradiation thereof. If a subject has a body thickness BT larger than the maximum body thickness BTmax, the control unit 22 of the radiation image capturing apparatus 1 cannot accurately detect start of irradiation thereof because the dose rate at which the radiation reaches the radiation image capturing apparatus 1 through the subject is too low.

It has also been found that even when radiation generation apparatuses 55 are set to emit radiation at the same dose rate, namely, the same tube voltage V is set to the radiation generation apparatuses 55, the radiation generation apparatuses 55 actually emit radiation at different dose rates because the irradiation characteristic varies among the radiation generation apparatuses 55. Accordingly, the maximum body thickness BTmax varies among the radiation generation apparatuses 55.

Hence, in the radiation image capturing system 50 of the present invention, in a case where any of radiation generation apparatuses 55 irradiates the radiation image capturing apparatus 1, the calculation unit calculates for each radiation generation apparatus 55 the maximum body thickness BTmax up to which the control unit 22 of the radiation image capturing apparatus 1 itself can detect start of irradiation thereof by the radiation generation apparatus 55 through a subject on the basis of the leak data dleak or the like read out in the radiation image capturing apparatus 1. The calculation process to calculate the maximum body thickness BTmax is performed before radiation image capturing and the information is stored.

With this configuration, although the irradiation characteristic varies among the radiation generation apparatuses 55, radiation image capturing can be performed by any of the radiation generation apparatus 55 on the basis of the pre-calculated condition which enables radiation image capturing with each radiation generation apparatus 55, namely, on the basis of information on the maximum body thickness BTmax for each radiation generation apparatus 55.

Accordingly, for example, the following problem can be prevented from arising for sure; although a radiation generation apparatus 55 emits radiation to a subject, the dose rate at which the radiation reaches the radiation image capturing apparatus 1 is so low that the control unit 22 of the radiation image capturing apparatus 1 cannot detect start of irradiation thereof, and consequently radiation needs to be emitted to the subject again to capture a radiation image of the subject and hence the exposed dose to the subject increases.

The calculation process is performed at the beginning when a radiation image capturing apparatus 1 and a radiation generation apparatus 55 are used in one radiation image capturing system 50; for example, when a radiation source 52 is newly installed in the radiation image capturing system 50 which performs radiation image capturing by using the radiation image capturing apparatus 1 (i.e. FPD) or when the radiation image capturing apparatus 1 is newly introduced into the radiation image capturing system 50 (in which a radiation generation apparatus 55 is already installed) which performs radiation image capturing by using a CR (Computed Radiography) apparatus or the like.

The maximum body thickness BTmax may be periodically calculated to be updated, for example, at the time of maintenance of the radiation generation apparatus 55.

According to the studies of the inventors of the present invention et al., it has also been found that the maximum body thickness BTmax may not only vary among the radiation generation apparatuses 55 but also vary depending on the dose rate at which a radiation generation apparatus 55 emits radiation or the tube voltage set to the radiation generation apparatus 55.

Hence, in the embodiment, the calculation unit calculates the maximum body thickness BTmax in relation to the tube voltage V set to the radiation generation apparatus 55, the maximum body thickness BTmax changing when the tube voltage V changes. That is, the calculation unit finds a relationship between the maximum body thickness BTmax and the tube voltage V.

Figure 15:
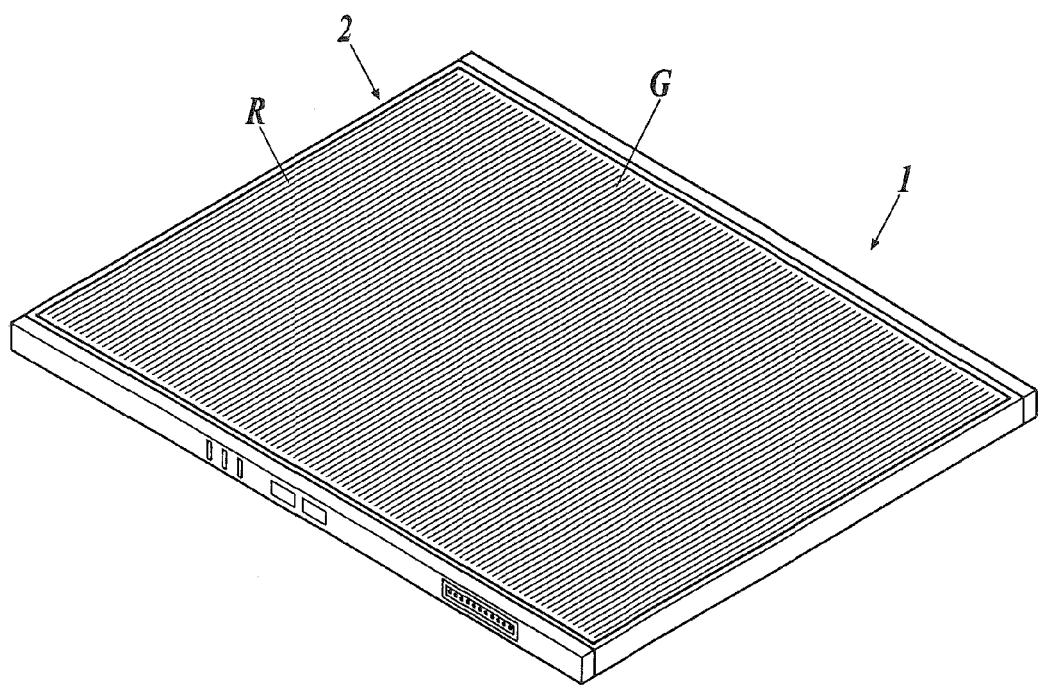
FIG. 15 is a perspective view showing the external appearance of the radiation image capturing apparatus with a grid attached.

Further, in order to prevent scattered radiation from entering the radiation image capturing apparatus 1, as shown in FIG. 15, radiation image capturing may be performed by the radiation image capturing apparatus 1 with a grid G set on the radiation incident surface R of the housing 2. The grid G absorbs a portion of radiation entering the radiation image capturing apparatus 1. Hence, even when the radiation generation apparatus 55 emits radiation to the radiation image capturing apparatus 1 with the grid G attached and to the radiation image capturing apparatus 1 with no grid G attached at the same dose rate, a dose rate at which the radiation enters the radiation image capturing apparatus 1 with the grid G attached is lower.

The lower the dose rate at which the radiation enters the radiation image capturing apparatus 1 is, the smaller the maximum body thickness BTmax is.

Hence, in the embodiment, the calculation unit finds the relationship between the maximum body thickness BTmax and the tube voltage V for the image capturing apparatus 1 with the grid G attached and for the radiation image capturing apparatus 1 with no grid G attached.

Figure 16:
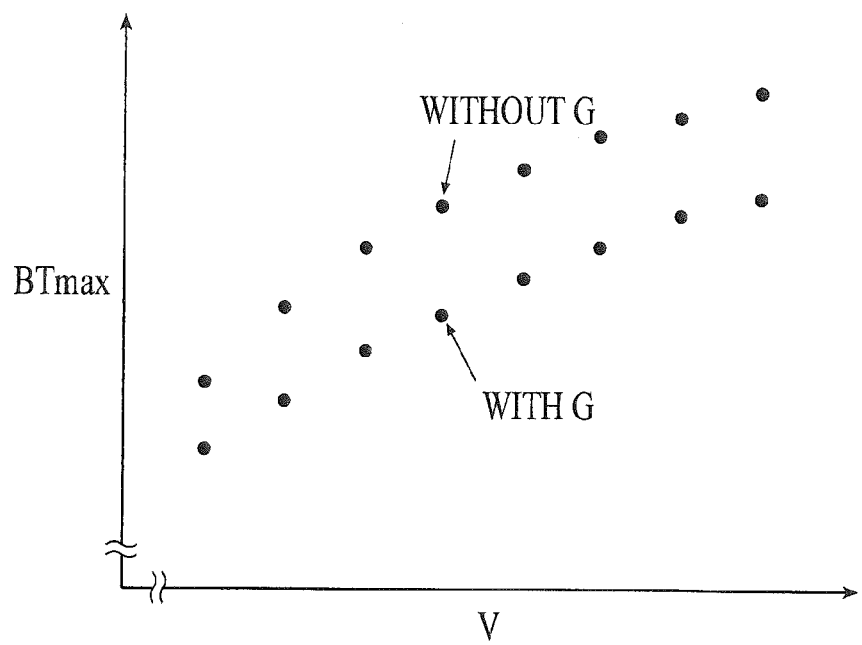
FIG. 16 is a graph showing an example of a relationship between a tube voltage and the maximum body thickness in a first embodiment.

In the embodiment, as shown in FIG. 16, the calculation unit changes the tube voltage V while making the radiation generation apparatus 55 emit radiation to the radiation image capturing apparatus 1 at a predetermined dose rate to determine whether or not the leak data dleak or the like read out in the radiation image capturing apparatus 1 is equal to or more than the threshold dleak th or the like at each tube voltage V and plot out the maximum body thickness BTmax.

As shown in FIG. 16, the calculation unit plots the maximum body thickness BTmax for the radiation image capturing apparatus 1 with no grid G attached ("Without G" in FIG. 16) and for the radiation image capturing apparatus 1 with the grid G attached ("With G" in FIG. 16). Thus, in the embodiment, the calculation unit calculates the maximum body thickness BTmax in relation to the tube voltage V, the change of which changes the maximum body thickness BTmax, taking existence or no existence of the grid G into account.

This calculation process is performed before radiation image capturing with respect to all the radiation generation apparatuses 55 existing in the radiation image capturing system 50 to find the above-described relationship (see FIG. 16) for each of the radiation generation apparatuses 55. If a plurality of radiation sources 52 are connected to one radiation generation apparatus 55, the above-described relationship (see FIG. 16) may be found for each of the radiation sources 52.

Here, the relationship shown in FIG. 16 is described more specifically. In a practical use, a relationship between the value of the leak data dleak or the like read out when the radiation generation apparatus 55 irradiates the radiation image capturing apparatus 1 with no subject therebetween and the maximum body thickness BTmax is known in advance.

Hence, a certain tube voltage V is set to a radiation generation apparatus 55 which is a target for finding the above-described relationship between the maximum body thickness BTmax and the tube voltage V, and the radiation generation apparatus 55 irradiates the radiation image capturing apparatus 1. The calculation unit calculates the maximum body thickness BTmax from the value of the leak data dleak or the like read out at the time in the radiation image capturing apparatus 1 to find the relationship shown in FIG. 16.

The dose rate at which the radiation generation apparatus 55 emits radiation at the set tube voltage V is determined in accordance with the irradiation characteristic of the radiation generation apparatus 55. Once the dose rate at which the radiation generation apparatus 55 emits radiation is determined, the dose rate at which the radiation reaches the radiation image capturing apparatus 1 from the radiation generation apparatus 55 is determined. The value of the leak data dlaek or the like read out in the radiation image capturing apparatus 1 is determined in accordance with the dose rate at which the radiation reaches the radiation image capturing apparatus 1, and the maximum body thickness BTmax is determined from the value of the leak data dleak or the like.

That is, once a relationship between the dose rate at which the radiation reaches the radiation image capturing apparatus 1 from the radiation generation apparatus 55 and the maximum body thickness BTmax calculated on the basis of the value of the leak data dleak or the like read out at that time is found by experiment, the maximum body thickness BTmax can be directly found from the dose rate at which the radiation reaches the radiation image capturing apparatus 1 from the radiation generation apparatus 55, without reading out the leak data dleak or the like any longer.

Hence, the calculation unit may perform the calculation process to calculate the maximum body thickness BTmax for each radiation generation apparatus 55 on the basis of data of a dose rate detected by a not-shown dosimeter (i) irradiated by the radiation generation apparatus 55 to which the tube voltage V is set and (ii) disposed at a position where the radiation image capturing apparatus 1 is disposed, instead of performing the calculation process on the basis of the value of the leak data dleak or the like read out in the radiation image capturing apparatus 1 irradiated by the radiation generation apparatus 55.

With this configuration, the relationship (see FIG. 16) between the tube voltage V and the maximum body thickness BTmax can be easily found. That is, the relationship between the tube voltage V, which is set to the radiation generation apparatus 55, and the maximum body thickness BTmax, which is calculated from the data of the does rate detected by the dosimeter irradiated by the radiation generation apparatus 55 to which the tube voltage V is set, can be found. In this case, it is unnecessary for the radiation image capturing apparatus 1 to be disposed at any position as long as the dosimeter is disposed at the position where the radiation image capturing apparatus 1 should be disposed.

In FIG. 16, the relationship between the tube voltage V and the maximum body thickness BTmax is shown in the form of a graph or a table in which values of the maximum body thickness BTmax are assigned to certain values of the tube voltage V. However, for example, curve approximation may be performed on the plotted points in FIG. 16 so that the maximum body thickness BTmax is expressed as a function of the tube voltage V.

In the case where the integration (detection method B) is adopted, the lower the dose rate at which the radiation reaches the radiation image capturing apparatus 1 is, the higher or longer the integration number or the integration time needs to be. Otherwise, the integrated value $\Sigma\Delta d$ of the differences $\Delta d(z)$ cannot be equal to or more than the threshold $\Sigma\Delta dth$, and accordingly start of irradiation of the radiation image capturing apparatus 1 cannot be detected.

Hence, when the integration (detection method B) is adopted as the irradiation start detection method, it is preferable that the integration number or the integration time of the differences $\Delta d(z)$ be increased as the dose rate at which the radiation reaches the radiation image capturing apparatus 1 decreases, namely, as the tube voltage V set to the radiation generation apparatus 55 becomes small or as the actual body thickness BT or the maximum body thickness BTmax becomes large.

[Area of Direct Irradiation Region of Radiation Image Capturing Apparatus Directly Irradiated by Radiation Generation Apparatus]

There is a case where the body thickness BT is so large that detection of start of irradiation of the radiation image capturing apparatus 1 is impossible at any tube voltages V settable to the radiation generation apparatus 55. There is also a case where the body thickness BT is relatively large and detection of start of irradiation thereof is possible at a high tube voltage V, but for some reason such as influence on a subject, irradiation at a high dose rate from the radiation generation apparatus 55 is not desired.

In these cases, if nothing is done, the control unit 22 of the radiation image capturing apparatus 1 cannot detect start of irradiation thereof, and accordingly radiation image capturing cannot be performed.

Then, in these cases, radiation is emitted in a state in which a region where the radiation image capturing apparatus 1 is directly irradiated by the radiation generation apparatus 55 not through a subject is formed so that radiation image capturing can be performed. Hereinafter, the region directly irradiated is referred to as a direct irradiation region.

As understood from the features of the detection methods 1 and 2 and the modified detection methods, namely, the calculus of finite differences (detection method A) and the integration (detection method B), the value of the leak data dleak read out from the direct irradiation region can be large. Accordingly, the control unit 22 of the radiation image capturing apparatus 1 can detect start of irradiation thereof.

Figure 17:
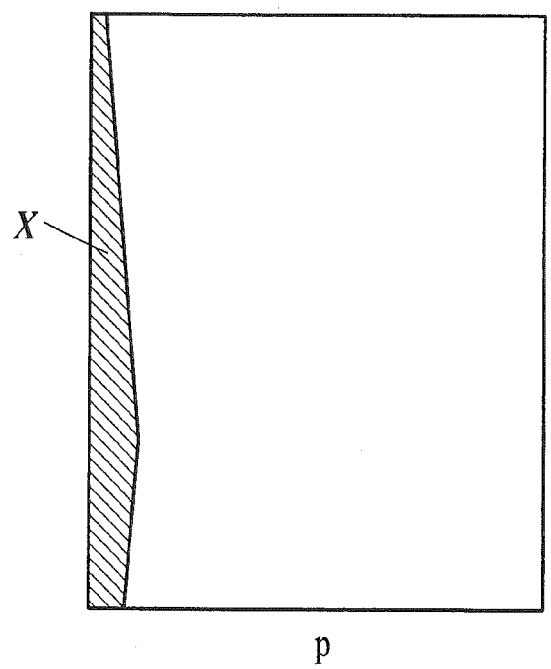
FIG. 17 is an illustration for explaining a region which is directly irradiated (direct irradiation region)

That is, in these cases, instead of radiation image capturing being performed in such a way that a subject is imaged to cover the whole area of a radiation image with no direct irradiation region, radiation image capturing is performed with the direct irradiation region X, which is directly irradiated not through a subject (patient) H, on the upper, lower, left or right portion outside a portion where the subject H is imaged in a radiation image p as shown in FIG. 17. To form the direct irradiation region X, the irradiation field to which the radiation generation apparatus 55 emits radiation is moved, or the subject H is moved to the left or right, for example.

In this way, for example, even when the body thickness BT is so large that detection of start of irradiation of the radiation image capturing apparatus 1 is impossible at any tube voltages V settable to the radiation generation apparatus 55 as described above, the control unit 22 of the radiation image capturing apparatus 1 can accurately detect start of irradiation thereof on the basis of the leak data dleak or the like read out from the direct irradiation region X. Accordingly, radiation image capturing can be appropriately performed.

As with the maximum body thickness BTmax, the area S of the direct irradiation region X varies. Even when radiation image capturing is performed with the direct irradiation region X as described above, if the area S of the direct irradiation region X is too small, the value of the read-out leak data dleak or the like changes too little, and hence the control unit 22 of the radiation image capturing apparatus 1 cannot detect start of irradiation thereof on the basis of the leak data dleak or the like.

That is, in the case where the direct irradiation region X is formed for radiation image capturing, the smallest area S to be ensured, namely, the minimum area Smin, exists for the direct irradiation region X. As described above, the irradiation characteristic varies among the radiation generation apparatuses 55. Hence, even when the same tube voltage V is set to the radiation generation apparatuses 55, the radiation generation apparatuses 55 actually emit radiation at different dose rates. Accordingly, the minimum value (the minimum area Smin) of the direct irradiation region X varies among the radiation generation apparatuses 55.

Hence, in the embodiment, before radiation image capturing, in addition to the maximum body thickness BTmax, the calculation unit calculates for each radiation generation apparatus 55 the direct irradiation region X, namely, the minimum area Smin down to which the control unit 22 of the radiation image capturing apparatus 1 can detect start of irradiation thereof with the direct irradiation region X.

With this configuration, as with the maximum body thickness BTmax, although the irradiation characteristic varies among the radiation generation apparatuses 55, radiation image capturing can be performed by any of the radiation generation apparatuses 55 on the basis of the pre-calculated condition which enables radiation image capturing with each radiation generation apparatus 55, namely, on the basis of information on the minimum area Smin for each radiation generation apparatus 55.

Hence, the radiation image capturing can be appropriately performed on the basis of the found condition even when the body thickness BT is so large that start of irradiation of the radiation image capturing apparatus 1 cannot be detected at any tube voltages V settable to the radiation generation apparatus 55. That is, the radiation image capturing can be appropriately performed with the direct irradiation region X having an area S equal to or more than the minimum area Smin. Accordingly, for example, the following problem can be prevented from arising for sure; radiation needs to be emitted to the same subject again to capture a radiation image of the subject and hence the exposed dose to the subject increases.

Figures 18, 19:
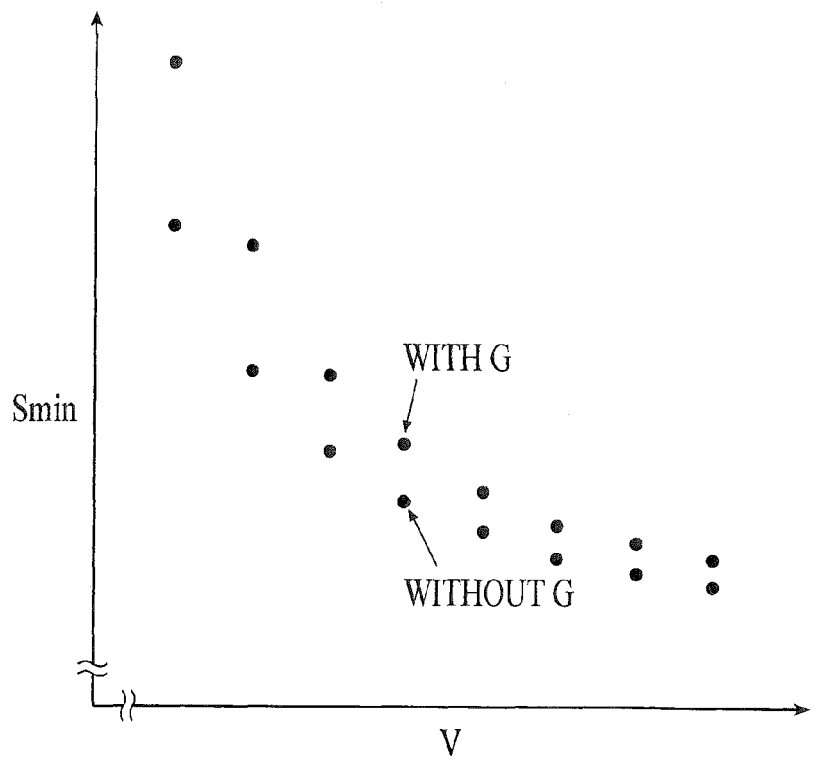
FIG. 18 is a graph showing an example of a relationship between the tube voltage and the minimum area of the direct irradiation region.
FIG. 19 is a table showing a result of performing a determination process multiple times at each sensitivity level of sensitivity for an irradiation start detection process in a second embodiment.

In the embodiment, as shown in FIG. 18, the calculation unit changes the tube voltage V, which is set to the radiation generation apparatus 55, and plots out the minimum area S for the radiation image capturing apparatus 1 with no grid G (see FIG. 15) attached ("Without G" in FIG. 18) and for the radiation image capturing apparatus 1 with the grid G attached ("With G" in FIG. 18).

Thus, in the embodiment, the calculation unit calculates the minimum area Smin in relation to the tube voltage V, the change of which changes the minimum area Smin, taking existence or no existence of the grid G into account.

This calculation process is performed before radiation image capturing with respect to all the radiation generation apparatuses 55 existing in the radiation image capturing system 50 to find the above-described relationship (see FIG. 18) for each of the radiation generation apparatuses 55. If a plurality of radiation sources 52 are connected to one radiation generation apparatus 55, the above-described relationship (see FIG. 18) may be found for each of the radiation sources 52.

In this case too, a relationship between the dose rate at which the radiation reaches the radiation image capturing apparatus 1 and the minimum area Smin can be found in advance, and the calculation process to find the above-described relationship between the minimum area Smin and the tube voltage V may be performed on the basis of data of a dose rate detected by a not-shown dosimeter (i) irradiated by the radiation generation apparatus 55 to which the tube voltage V is set and (ii) disposed at a position where the radiation image capturing apparatus 1 is disposed. In this case, it is unnecessary for the radiation image capturing apparatus 1 to be disposed at any position as long as the dosimeter is disposed at the position where the radiation image capturing apparatus 1 should be disposed.

In FIG. 18, the relationship between the tube voltage V and the minimum area Smin is shown in the form of a graph or a table in which values of the minimum area Smin are assigned to certain values of the tube voltage V. However, for example, curve approximation may be performed on the plotted points in FIG. 18 so that the minimum area Smin is expressed as a function of the tube voltage V.

[Factors Other than Tube Voltage V]

As described above, whether or not the control unit 22 of the radiation image capturing apparatus 1 can detect start of irradiation thereof depends on the dose rate at which the radiation generation apparatus 55 emits radiation. In the radiation image capturing system 50 of the embodiment, the dose rate at which the radiation generation apparatus 55 emits radiation mainly depends on the tube voltage V set to the radiation generation apparatus 55.

Hence, in the embodiment, the relationship between the tube voltage V and the maximum body thickness BTmax and the relationship between the tube voltage V and the minimum area Smin are found.

However, if the tube current I set to the radiation generation apparatus 55 can be set by an operator, and the dose rate at which the radiation generation apparatus 55 emits radiation depends on the tube current I, a relationship with the maximum body thickness BTmax and a relationship with the minimum area Smin may be found by changing the tube current I in addition to the tube voltage V.

Further, if the distance L between the radiation generation apparatus 55 and the radiation image capturing apparatus 1 is changeable, the dose rate at which the radiation reaches the radiation image capturing apparatus 1 changes depending on the distance L even when the radiation generation apparatus 55 emits radiation at the same dose rate before and after the distance L changes.

In particular, in the case where the portable radiation generation apparatus 55 is used in the radiation image capturing system 50 as shown in FIG. 5, it is difficult to use the radiation image capturing system 50 with the distance L between the radiation source 52P and the radiation generation apparatus 55 fixed, and usually the distance L changes each time radiation image capturing is performed. Hence, in the case of the portable radiation generation apparatus 55 in particular, even when the radiation generation apparatus 55 emits radiation at the same dose rate, the dose rate at which the radiation reaches the radiation image capturing apparatus 1 easily changes.

Hence, if the distance L is changeable, a relationship with the maximum body thickness BTmax and a relationship with the minimum area Smin may be found by changing the distance L in addition to the tube voltage V and/or the like.

Thus, in the embodiment, when there are other factors than the tube voltage V to change the dose rate at which the radiation reaches the radiation image capturing apparatus 1, it is preferable to find the relationship with the maximum body thickness BTmax and the relationship with the minimum area Smin by changing the radiography condition including any of these factors in addition to the tube voltage V.

In the following, to make the explanation simple, as the radiography condition, only the tube voltage V (radiography condition) set to the radiation generation apparatus 55 is changed. However, the present invention is not limited to the case and hence, as described above, can be applied to any case where the radiography condition including any factors to change the dose rate at which the radiation reaches the radiation image capturing apparatus 1 is changed.

[Application of Body Thickness BT of Subject and Area S of Direct Irradiation Region]

Next, how to use the information on the maximum body thickness BTmax (see FIG. 16) and the minimum area Smin (see FIG. 18), which are calculated by the calculation unit, in the radiation image capturing system 50 is described. In the following, several examples thereof are described.

[First Application]

The most direct way of using the information on the maximum body thickness BTmax and the minimum area S calculated by the calculation unit is, for example, using the information by printing out the information in the form of graphs as shown in FIGS. 16 and 18 or tables or displaying the information on a display unit of a computer such as the display unit 58a of the console 58 (see FIG. 4 or 5) in the radiation image capturing system 50.

More specifically, for example, an operator measures or estimates with his/her eyes the actual body thickness BT of a subject or obtains information on the body thickness BT of a patient recorded as patient information, calculates a tube voltage V to be set to the radiation generation apparatus 55 on the basis of the relationship (see FIG. 16) between the maximum body thickness BTmax and the tube voltage V printed out or displayed on the display unit and sets the calculated tube voltage V (radiography condition) to the radiation generation apparatus 55.

That is, in the case of the first application, an operator manually adjusts the radiography condition including the tube voltage V on the basis of the information on the maximum body thickness BTmax (see FIG. 16) calculated by the calculation unit and sets the radiography condition including a selected tube voltage V to the radiation generation apparatus 55.

If the actual body thickness BT of a subject is more than the maximum body thickness BTmax no matter what tube voltage V is set to the radiation generation apparatus 55, the operator decides what (value of) area S of the direct irradiation region X should be set on the basis of the relationship between the minimum area Smin and the tube voltage V (see FIG. 18).

Then, radiation is emitted in a state in which the direct irradiation region X having the decided area S is formed so that radiation image capturing can be performed.

[Second Application]

As described above, in the embodiment, a radiography condition such as a tube voltage V to be set to the radiation generation apparatus 55 can be input on the console 58. How to input the radiography condition is not particularly limited, and hence a known input way can be adopted therefor. For example, an operator inputs a radiography condition such as a tube voltage V with the input unit such as a mouse or a keyboard (both not shown) of the console 58.

Alternatively, the console 58 may automatically input a radiography condition such as a tube voltage V suitable for a radiography part into itself on the basis of a radiography part, such as "Front Chest (chest from the front)", specified in radiography order information when an operator inputs the radiography order information into the console 58 from an HIS (Hospital Information System) or a RIS (Radiology Information System) connected to the console 58 via a not-shown network.

Further, a radiography condition such as a tube voltage V may be written and set in the radiography order information in advance. Then, at the same time the console 58 obtains the radiography order information, the radiography condition can be input into the console 58.

In the embodiment, when a radiography condition is input into the console 58 as described above, the console 58 sends and sets the radiography condition to the radiation generation apparatus 55 (see FIG. 4 or 5). Then, as described above, the radiation generation apparatus 55 controls the radiation source 52 to emit radiation at an appropriate radiation dose or dose rate on the basis of the set radiography condition, for example, by supplying a set tube voltage V to the radiation source 52.

In this second application, when a radiography condition is input into the console 58, the information on the actual body thickness BT of a subject is also input into the console 58 as the radiography condition.

The actual body thickness BT of a subject can be obtained and input into the console 58 in the same way described above, namely, for example; an operator measures or estimates with his/her eyes the actual body thickness BT of a subject and inputs the information on the actual body thickness BT into the console 58, or the information on the body thickness BT of a patient recorded as patient information is obtained from the HIS or RIS described above and input into the console 58. In any of the application described below too, the information on the actual body thickness BT of a subject is obtained and input into the console 58 in the same way.

In the second application, the radiation image capturing system 50 includes a notifying unit. The notifying unit notifies that the actual body thickness BT input into the console 58 is more than the maximum body thickness BTmax under the radiography condition (tube voltage V, for example) input into the console 58, so that the control unit 22 of the radiation image capturing apparatus 1 cannot detect start of irradiation thereof under the input radiography condition.

The console 58 may be used as the notifying unit, or not the console 58 but another component may be provided as the notifying unit. As a notifying way, indications, sounds, vibrations or the like can be adopted. The notifying way is not particularly limited as long as an operator can be notified that, under the set radiography condition, start of irradiation of the radiation image capturing apparatus 1 cannot be detected and radiation image capturing cannot be performed.

The operator to whom the message is notified changes the radiography condition such as the tube voltage V and inputs and sets the changed radiography condition to the console 58 or performs an operation to form the direct irradiation region X in order that the control unit 22 of the radiation image capturing apparatus 1 can accurately detect start of irradiation thereof, and radiation image capturing is performed.

[Third Application]

In the above-described second application, the notifying unit (console 58 in the above example) determines whether or not a subject having a body thickness BT input by an operator can be imaged under an input radiography condition such as an input tube voltage V and notifies the determination result.

Instead of an operator inputting the actual body thickness BT of a subject into the console 58, the notifying unit may notify the maximum body thickness BTmax up to which the control unit 22 of the radiation image capturing apparatus 1 can detect start of irradiation thereof under an input radiography condition such as an input tube voltage V.

That is, when a radiography condition is input into the console 58 as described above or the console 58 automatically inputs a radiography condition into itself on the basis of the information on a radiography part and the like specified in the radiography order information obtained from the HIS or RIS, the notifying unit (console 58, for example) finds the maximum body thickness BTmax up to which the control unit 22 of the radiation image capturing apparatus 1 can detect start of irradiation thereof under the radiography condition input into the console 58 on the basis of the information on the maximum body thickness BTmax calculated by the calculation unit and notifies the found maximum body thickness BTmax.

An operator looks at the maximum body thickness BTmax notified by the notifying unit, and if the actual body thickness BT of a subject is equal to or less than the notified maximum body thickness BTmax, does not change the radiography condition input into the console 58 and sends and sets the radiography condition to the radiation generation apparatus 55.

On the other hand, if the actual body thickness BT of a subject is more than the notified maximum body thickness BTmax, the operator changes the radiography condition such as the tube voltage V or performs an operation to form the direct irradiation region X in order that the control unit 22 of the radiation image capturing apparatus 1 can accurately detect start of irradiation thereof, and radiation image capturing is performed.

[Fourth Application]

In the above-described first application to third application, regardless of the actual body thickness BT of a subject, an operator inputs a radiography condition into the console 58 or the console 58 automatically inputs a radiography condition into itself on the basis of the information on a radiography part and the like specified in the radiography order information. Instead, for example, the notifying unit may notify an appropriate radiography condition on the basis of the actual body thickness BT of a subject input by an operator.

That is, when, for example, an operator measures or estimates with his/her eyes the actual body thickness BT of a subject and inputs the information on the actual body thickness BT into the notifying unit, or the information on the body thickness BT of a subject is obtained from the HIS or RIS, the notifying unit finds a radiography condition (tube voltage V, for example) under which the control unit 22 of the radiation image capturing apparatus 1 can detect start of irradiation thereof through the subject having the actual body thickness BT on the basis of the relationship shown in FIG. 16, namely, the relationship between the radiography condition (tube voltage V, for example) set to the radiation generation apparatus 55 and the maximum body thickness BTmax which changes when the radiography condition changes and notifies the found radiography condition.

The operator inputs the radiography condition notified by the notifying unit into the console 58, and the console 58 sends and sets the radiography condition to the radiation generation apparatus 55.

If no appropriate radiography condition is notified by the notifying unit (i.e. radiation image capturing cannot be performed) or the radiography condition notified by the notifying unit makes the dose rate at which the radiation generation apparatus 55 emits radiation to the subject too large, the operator changes the radiography condition such as the tube voltage V or performs an operation to form the direct irradiation region X in order that the control unit 22 of the radiation image capturing apparatus 1 can accurately detect start of irradiation thereof, and radiation image capturing is performed.

[Fifth Application]

In the above-described fourth application, the notifying unit finds and notifies an appropriate radiography condition on the basis of an obtained actual body thickness BT of a subject. Instead, the console 58 may find an appropriate radiography condition (tube voltage V, for example) under which the control unit 22 of the radiation image capturing apparatus 1 can detect start of irradiation thereof through a subject having an obtained actual body thickness BT on the basis of the relationship between the radiography condition (tube voltage V, for example) set to the radiation generation apparatus 55 and the maximum body thickness BTmax which changes when the radiography condition changes and automatically set the found radiography condition to the radiation generation apparatus 55 without notifying the found radiography condition to an operator.

If, under any radiography conditions, radiation image capturing cannot be performed through the subject having the actual body thickness BT obtained by the console 58, such a message is notified to an operator through an indication on the display unit 58a of the console 58 or a sound, for example.

The operator can monitor the radiography condition automatically set by the console 58 as needed. Hence, if the radiography condition automatically set by the console 58 makes the dose rate at which the radiation generation apparatus 55 emits radiation to the subject too large, the operator can appropriately change the radiography condition on the console 58.

If necessary, the operator performs an operation to form the direct irradiation region X in order that the control unit 22 of the radiation image capturing apparatus 1 can accurately detect start of irradiation thereof, and radiation image capturing is performed.

[Advantageous Effects]

As described above, according to the radiation image capturing system 50 of the embodiment, before radiation image capturing, the calculation unit calculates the maximum body thickness BTmax for each radiation generation apparatus 55 on the basis of data such as the leak data dleak read out in the radiation image capturing apparatus 1 irradiated by the radiation generation apparatus 55, the maximum body thickness BTmax up to which the control unit 22 of the radiation image capturing apparatus 1 can detect start of irradiation thereof through a subject.

Accordingly, although the irradiation characteristic varies among the radiation generation apparatuses 55, the condition which enables radiation image capturing using each radiation generation apparatus 55, namely, the maximum body thickness BTmax for each radiation generation apparatus 55, is found in advance.

Hence, even when, for example, a first radiation generation apparatus 55 which irradiates the radiation image capturing apparatus 1 is replaced by a second radiation generation apparatus 55, whether or not the actual body thickness BT of a subject is equal to or less than the maximum body thickness BTmax can be correctly determined on the basis of the found condition for the second radiation generation apparatus 55, and hence the radiation image capturing apparatus 1 can accurately detect start of irradiation thereof and appropriately perform radiation image capturing.

Accordingly, for example, the following problem can be prevented from arising for sure; although a radiation generation apparatus 55 emits radiation to a subject, the dose rate at which the radiation reaches the radiation image capturing apparatus 1 from the radiation generation apparatus 55 is so low that the control unit 22 of the radiation image capturing apparatus 1 cannot detect start of irradiation thereof, and consequently radiation needs to be emitted to the subject again to capture a radiation image of the subject and hence the exposed dose to the subject increases.

In the embodiment, as described above, because the irradiation characteristic varies among the radiation generation apparatuses 55, the maximum body thickness BTmax and the like are calculated for each radiation generation apparatus 55.

In the embodiment, it is assumed that the maximum body thickness BTmax and the like remain the same regardless of the radiation image capturing apparatuses 1, so that the above-described calculation processes are not performed for each radiation image capturing apparatus 1.

However, there are various sizes of radiation image capturing apparatuses 1, such as 14 in.×17 in., 14 in.×14 in., and 17 in.×17 in. It is possible that the maximum body thickness BTmax or the like changes depending on the size of a radiation image capturing apparatus 1. It is also possible that the maximum body thickness BTmax or the like changes when any of the specifications of a radiation image capturing apparatus 1 changes.

Hence, the relationship (see FIG. 16 or 18) between the maximum body thickness BTmax or the like and the radiography condition such as the tube voltage V may be found in advance for each radiation image capturing apparatus 1 or whenever any of the specifications of a radiation image capturing apparatus 1 changes.

Further, it is possible that the relationship between the maximum body thickness BTmax or the like and the radiography condition such as the tube voltage V changes as the time passes because of deterioration over time, such as the frequency of use or the used period, of the radiation image capturing apparatus 1.

Hence, the relationship may be found again, for example, at the time of calibration of the radiation image capturing apparatus 1 to be updated. Updating the relationship over time can certainly prevent the control unit 22 of the radiation image capturing apparatus 1 from not being able to detect start of irradiation thereof although the radiation generation apparatus 55 irradiates the radiation image capturing apparatus 1 through a subject.

Second Embodiment

In the above-described first embodiment, it is assumed that the control unit 22 of the radiation image capturing apparatus 1 performs the irradiation start detection process at only one level (sensitivity level) of sensitivity. However, as described below, the sensitivity for the irradiation start detection process can be changed, for example, by changing the thresholds in the above-described detection methods.

[Sensitivity for Irradiation Start Detection Process]

In the radiation image capturing apparatus 1 of a second embodiment of the present invention, when the irradiation start detection process is performed by using the above-described calculus of finite differences (detection method A), integration (detection method B) or the like, the sensitivity of the control unit 22 for the irradiation start detection process is changed as needed and set. In the embodiment, the sensitivity therefor is changed by changing the threshold $\Delta$dth in the calculus of finite differences and/or the threshold $\tau\Delta$dth in the integration.

More specifically, when radiation emitted from the radiation generation apparatus 55 (see FIG. 4 or 5) to the radiation image capturing apparatus 1 is sufficiently strong (i.e. the dose rate at which the radiation is emitted is high), the radiation image capturing apparatus 1 can detect start of irradiation thereof well even if the sensitivity for the irradiation start detection process is low, and hence the threshold $\Delta$dth and/or the threshold $\tau\Delta$dth are each changed to a higher value to decrease the sensitivity. The sensitivity level in this case is referred to as the "low sensitivity".

On the other hand, when radiation emitted from the radiation generation apparatus 55 to the radiation image capturing apparatus 1 is weak (i.e. the dose rate at which the radiation is emitted is low), the threshold $\Delta$dth and/or the threshold $\Sigma\Delta$dth are each changed to a lower value to increase the sensitivity. The sensitivity level in this case is referred to as the "high sensitivity".

Thus, in the radiation image capturing apparatus 1, the sensitivity for the irradiation start detection process is changed by changing the threshold $\Delta$dth in the calculus of finite differences and/or the threshold $\tau\Delta$dth in the integration.

When the radiography condition is for making radiation emitted to the radiation image capturing apparatus 1 sufficiently strong, namely, the leak data dleak or the like read out therein is large and the difference (or differences) $\Delta$d(z) based thereon is sufficiently large, start of irradiation thereof can be detected well by using only the calculus of finite differences (detection method A), not using the integration (detection method B).

Hence, in the embodiment, when the irradiation start detection process is performed at the "low sensitivity", the threshold $\tau\Delta$dth in the integration (detection method B) is set to a very high value, so that start of irradiation of the radiation image capturing apparatus 1 cannot be actually detected by the integration (detection method B). Consequently, the irradiation start detection process is performed by using only the calculus of finite differences (detection method A) based on the difference $\Delta$d(z).

With this configuration, the control unit 22 of the radiation image capturing apparatus 1 performs the irradiation start detection process by determining whether or not the difference $\Delta$d(z) is equal to or more than the threshold $\Delta$dth by actually using only the calculus of finite differences. Accordingly, the load of the irradiation start detection process can be light. The threshold $\Delta$dth for the "low sensitivity" is set to a higher value than that for the "high sensitivity".

In the embodiment, the "middle sensitivity" is provided between the "low sensitivity" and the "high sensitivity". The threshold $\Delta$dth in the calculus of finite differences (detection method A) for the "middle sensitivity" is set to a lower value than that for the "low sensitivity" so that the "middle sensitivity" is higher than the "low sensitivity". The threshold $\Sigma\Delta$dth in the integration (detection method B) for the "middle sensitivity" is set to a very high value, so that as with the "low sensitivity", the irradiation start detection process is not actually performed by the integration.

In the embodiment, the "high sensitivity" is set when radiation is emitted to the radiation image capturing apparatus 1 at a very low dose rate for radiation image capturing, such as radiation image capturing of auditory organs with the Schuller method.

The threshold $\Sigma\Delta$dth in the integration (detection method B) for the "high sensitivity" is set to a low value, so that the irradiation start detection process is performed by using both the calculus of finite differences (detection method A) and the integration (detection method B). In the embodiment, at the "high sensitivity", the control unit 22 of the radiation image capturing apparatus 1 can detect start of irradiation thereof when the data is equal to or more than the threshold in either the calculus of finite differences or the integration.

The sensitivity for the irradiation start detection process may be divided into more sensitivity levels to set.

The way for changing the sensitivity for the irradiation start detection process performed by the radiation image capturing apparatus 1 is not limited to changing the thresholds as described in the embodiment. For example, the sensitivity may be changed, for example, by changing a collection period to collect the leak data dleak or the data d for irradiation start detection to make the magnitude of the value thereof read out by performing the data readout process one time larger or smaller.

In the embodiment, the calculation unit finds the relationship between the tube voltage V and the maximum body thickness BTmax shown in FIG. 16 for each sensitivity level in advance. In the embodiment, the console 58 stores the relationship for each sensitivity level found by the calculation unit in a storage unit 59 (see FIG. 4), for example. In this case too, the relationship is found and stored for each radiation generation apparatus 55.

[Changing with Console Sensitivity for Irradiation Start Detection Process Performed by Radiation Image Capturing Apparatus]

In the embodiment, the console 58 (see FIG. 4 or 5) sends signals to the radiation image capturing apparatus 1 to change the sensitivity of the control unit 22 of the radiation image capturing apparatus 1 for the irradiation start detection process.

The simplest configuration therefor is that when an operator inputs a sensitivity level for the irradiation start detection process desired to be set to the radiation image capturing apparatus 1 into the console 58, the console 58 sends to the radiation image capturing apparatus 1 a signal to change the sensitivity to the set sensitivity level. In response to the signal, the control unit 22 of the radiation image capturing apparatus 1 changes the threshold $\Delta$dth in the calculus of finite differences and/or the threshold $\Sigma\Delta$dth in the integration to change the sensitivity and performs the irradiation start detection process at the set sensitivity level.

A more complicated configuration therefor is, for example, that when an operator measures or estimates with his/her eyes the actual body thickness BT of a subject and inputs the information on the actual body thickness BT into the console 58, or the information on the actual body thickness BT of a subject is obtained from the HIS or RIS described above, the console 58 finds on the basis of the above-described relationship a sensitivity level(s) at which the control unit 22 of the radiation image capturing apparatus 1 can detect start of irradiation thereof under an input radiography condition (tube voltage V, for example) through the subject having the actual body thickness BT.

If there is only one sensitivity level among the sensitivity levels, the one sensitivity level (the "high sensitivity" in the case where the three sensitivity levels of the "high sensitivity", "middle sensitivity" and "low sensitivity" are provided) at which the control unit 22 of the radiation image capturing apparatus 1 can detect start of irradiation thereof, the console 58 sends to the radiation image capturing apparatus 1 a signal to change the sensitivity to that one sensitivity level.

On the other hand, if there are a plurality of sensitivity levels among the sensitivity levels, the plurality of sensitivity levels at which the control unit 22 of the radiation image capturing apparatus 1 can detect start of irradiation thereof, the console 58 selects a sensitivity level under a preset condition, such as a sensitivity level which is the highest among the usable sensitivity levels, a sensitivity level at which start of irradiation thereof can be detected in a state in which the S/N ratio is good or a sensitivity level at which power consumption in the radiation image capturing apparatus 1 is the least, and sends to the radiation image capturing apparatus 1 a signal to change the sensitivity to the selected sensitivity level.

In this case too, in response to the received signal, the control unit 22 changes both or one of the thresholds to change the sensitivity and performs the irradiation start detection process at the found (selected) sensitivity level.

With this configuration, for example, even when the radiation image capturing apparatus 1 is carried from a radiography room R1 to another radiography room R1, and the radiography condition changes, for example, a first radiation generation apparatus 55 which irradiates the radiation image capturing apparatus 1 is replaced by a second radiation generation apparatus 55, the console 58 finds a sensitivity level(s) at which the control unit 22 of the radiation image capturing apparatus 1 can accurately detect start of irradiation thereof by the second radiation generation apparatus 55 through a subject having a body thickness BT, and makes the radiation image capturing apparatus 1 change the sensitivity to the found sensitivity level, thereby appropriately changing the state of the radiation image capturing apparatus 1.

Thus, the control unit 22 of the radiation image capturing apparatus 1 performs the irradiation start detection process at the found sensitivity level, and accordingly can accurately detect start of irradiation thereof by the second radiation generation apparatus 55 and appropriately perform radiation image capturing.

In general, the portable radiation generation apparatus 55 (see FIG. 5), which is used to irradiate the radiation image capturing apparatus 1, emits radiation at a lower dose rate than that of the fixed radiation generation apparatus 55 (see FIG. 4) fixed to the radiography room R1.

In addition, while the distance L between the fixed radiation generation apparatus 55 and the radiation image capturing apparatus 1 is fixed to some extent, the distance L between the potable radiation generation apparatus 55 and the radiation image capturing apparatus 1 at the time of use greatly changes. That is, the range of values (distances L) of the distance L between the potable radiation generation apparatus 55 and the radiation image capturing apparatus 1 to be short or long is wide.

Hence, in the case where the portable radiation generation apparatus 55 is disposed relatively apart from the radiation image capturing apparatus 1, even when a predetermined tube voltage V is set to the portable radiation generation apparatus 55 to emit radiation to the radiation image capturing apparatus 1 at a certain dose rate, the dose rate at which the radiation actually reaches the radiation image capturing apparatus 1 may be much lower than a predetermined dose rate.

Then, if it is known in advance that the portable radiation generation apparatus 55 is used to irradiate the radiation image capturing apparatus 1, as a signal to change the sensitivity for the irradiation start detection process, the console 58 sends to the radiation image capturing apparatus 1 a signal to change the sensitivity to a sensitivity level which is one level higher than that to be set to the fixed radiation generation apparatus 55 when the fixed radiation generation apparatus 55 is used to irradiate the radiation image capturing apparatus 1.

That is, for example, in the case where the "low sensitivity" is set to the fixed radiation generation apparatus 55 when the fixed radiation generation apparatus 55 is used to irradiate the radiation image capturing apparatus 1, the console 58 sends to the radiation image capturing apparatus 1 a signal to change the sensitivity to the "middle sensitivity" when the portable radiation generation apparatus 55 is used to irradiate the radiation image capturing apparatus 1. Also, in the case where the "middle sensitivity" is set to the fixed radiation generation apparatus 55 when the fixed radiation generation apparatus 55 is used to irradiate the radiation image capturing apparatus 1, the console 58 sends to the radiation image capturing apparatus 1 a signal to change the sensitivity to the "high sensitivity" when the portable radiation generation apparatus 55 is used to irradiate the radiation image capturing apparatus 1.

However, if it is known in advance that at what dose rate the portable radiation generation apparatus 55 emits radiation on the basis of, for example, a set tube voltage V and the information on a radiography part of a subject and the like, and the dose rate is sufficiently high, it is unnecessary to make the sensitivity one level higher than that set to the fixed radiation generation apparatus 55.

Hence, for example, the console 58 may determine whether or not to make the sensitivity one level higher on the basis of a radiography condition such as a tube voltage V to be set to the portable radiation generation apparatus 55 and the information on a radiography part of a subject and the like. Alternatively, in order to obtain operator's determination thereon, a request may be made (notified) to the operator to input an instruction to make the sensitivity one level higher or an instruction not to make the sensitivity one level higher.

With this configuration, even when the fixed radiation generation apparatus 55 is replaced by the portable radiation generation apparatus 55, the console 58 finds a sensitivity level(s) at which the control unit 22 of the radiation image capturing apparatus 1 can accurately detect start of irradiation thereof by the portable radiation generation apparatus 55 through a subject having a body thickness BT, and makes the radiation image capturing apparatus 1 change the sensitivity to the found sensitivity level, thereby appropriately changing the state of the radiation image capturing apparatus 1.

Thus, in this case too, the control unit 22 of the radiation image capturing apparatus 1 performs the irradiation start detection process at the found sensitivity level, and accordingly can accurately detect start of irradiation thereof by the portable radiation generation apparatus 55 and appropriately perform radiation image capturing.

[Advantageous Effects]

As described above, according to the radiation image capturing system 50 of the embodiment, even when the radiography condition changes, for example, a first radiation generation apparatus 55 is replaced by a second radiation generation apparatus 55, the console 58 finds a sensitivity level(s) at which the control unit 22 of the radiation image capturing apparatus 1 can accurately detect start of irradiation thereof by the second radiation generation apparatus 55 through a subject having a body thickness BT, and makes the radiation image capturing apparatus 1 change the sensitivity to the found sensitivity level, thereby appropriately changing the state of the radiation image capturing apparatus 1.

Thus, the control unit 22 of the radiation image capturing apparatus 1 performs the irradiation start detection process at the found sensitivity level, and accordingly can accurately detect start of irradiation thereof by the second radiation generation apparatus 55 and appropriately perform radiation image capturing.

In the embodiment, when the body thickness BT of a subject is so large that the control unit 22 of the radiation image capturing apparatus 1 cannot detect start of irradiation thereof no matter to which sensitivity level the control unit 22 changes the sensitivity, such a message is notified to an operator through an indication on the display unit 58a (see FIG. 4 or 5) of the console 58 or a sound, for example.

Third Embodiment

False Detection Due to Radio Waves, Impacts, Etc.

In the above-described first and second embodiments, explanation is mainly made regarding the case where the control unit 22 of the radiation image capturing apparatus 1 cannot detect start of irradiation thereof although the radiation generation apparatus 55 irradiates the radiation image capturing apparatus 1 because a patient as a subject is fat, and hence the body thickness BT of the subject is so large that the dose rate at which the radiation reaches the radiation image capturing apparatus 1 is low.

Meanwhile, as described above, according to the studies of the inventors of the present invention et al., it has been found that the radiation image capturing apparatus 1 may falsely detect start of irradiation thereof although the radiation image capturing apparatus 1 is not actually irradiated because of influence of radio waves emitted by, for example, an apparatus such as the radiation generation apparatus 55 in the radiography room R1; or impacts, vibrations or the like added to the radiation image capturing apparatus 1 by the radiation image capturing apparatus 1 moving during radiation image capturing, which can be seen at some radiography tables.

It has also been found that the radiation image capturing apparatus 1 may falsely detect start of irradiation thereof because of influence of impacts, vibrations or the like added to the radiation image capturing apparatus 1 by the radiation image capturing apparatus 1 and a patient's body, the bed B or the like hitting each other when the radiation image capturing apparatus 1 is not set on the Bucky device 51 (see FIG. 4) but placed on the patient's body or inserted between the patient's body and the bed B or the like as shown in FIG. 5.

According to the studies of the inventors of the present invention et al., it has been found that as with the second embodiment, when the control unit 22 of the radiation image capturing apparatus 1 changes the sensitivity for the irradiation start detection process by changing the threshold Δdth in the calculus of finite differences and/or the threshold ΣΔdth in the integration, the control unit 22 thereof may hardly be influenced by the above-described radio waves, impacts or the like, for example, by changing the thresholds to change the sensitivity, and accordingly can accurately detect start of irradiation thereof.

Hence, in the radiation image capturing system 50 of a third embodiment, explanation is made regarding the configuration and the like with which even when the radiation image capturing apparatus 1 is used under the operating environment where the radiation image capturing apparatus 1 may falsely detect start of irradiation thereof because of the radio waves, impacts or the like, the radiation image capturing apparatus 1 can be appropriately adjusted, and hence the control unit 22 of the radiation image capturing apparatus 1 does not falsely detect start of irradiation thereof but can accurately detect start of irradiation thereof.

[Setting Sensitivity not to Cause False Detection Etc.]

It is not always easy to predict what kind of or how much impact or the like is added to the radiation image capturing apparatus 1 by the radiation image capturing apparatus 1 and the patient's body, the bed B or the like hitting each other, by which the radiation image capturing apparatus 1 falsely detects start of irradiation thereof. However, it is not difficult to predict what kind of or how much radio wave is emitted from, for example, an apparatus such as the radiation generation apparatus 55 in a radiography room or what kind of or how much impact or the like is added to the radiation image capturing apparatus 1 from a radiography table or the like, during radiation image capturing.

Hence, as described above, in the case where the control unit 22 of the radiation image capturing apparatus 1 can change the sensitivity for the irradiation start detection process, a sensitivity level can be found in advance, the sensitivity level (condition) at which the control unit 22 thereof can accurately detect start of irradiation thereof even when the radiation image capturing apparatus 1 picks up radio waves, or even when impacts or the like are added to the radiation image capturing apparatus 1 from an apparatus or the like.

More specifically, as with the calculation unit described in the first embodiment, the radiation image capturing system 50 of the third embodiment includes a determination unit. The determination process performed by the determination unit may be performed by the console 58 (i.e. the console 58 functions as the determination unit) or by a computer such as a not-shown image processing apparatus in the radiation image capturing system 50. Alternatively, a specialized computer as the determination unit may be provided.

In order to find out only the influence of the radio waves, impacts or the like added to the data read out in the radiation image capturing apparatus 1 such as the leak data dleak, unlike the calculation process to calculate the maximum body thickness BTmax performed by the calculation unit of the first embodiment, the determination process performed by the determination unit of the third embodiment is performed before radiation image capturing without irradiation of the radiation image capturing apparatus 1.

When determination is made on the influence on the radiation image capturing apparatus 1 caused by irradiation thereof, such as radio waves emitted when the radiation generation apparatus 55 emits radiation, the determination unit performs the determination process while making the radiation generation apparatus 55 actually emit radiation but not irradiate the radiation image capturing apparatus 1. The "radiation image capturing apparatus not irradiated" includes such a state, namely, the state in which radiation is emitted, but the radiation image capturing apparatus 1 is not irradiated with the radiation.

While changing the sensitivity of the control unit 22 of the radiation image capturing apparatus 1 for the irradiation start detection process, the determination unit determines whether or not the calculated difference $\Delta d(z)$ in the calculus of finite differences or the calculated integrated value $\Sigma \Delta d$ of the differences $\Delta d(z)$ in the integration is equal to or more than the threshold $\Delta dth$ or the threshold $\Sigma \Delta dth$ at each sensitivity level.

If the difference $\Delta d(z)$ or the integrated value $\Sigma \Delta d$ calculated in this state is equal to or more than the threshold $\Delta dth$ or the threshold $\Sigma \Delta dth$, start of irradiation of the radiation image capturing apparatus 1 is detected although the radiation image capturing apparatus 1 is not irradiated. In other words, start of irradiation thereof is falsely detected.

In the embodiment, the determination process is performed multiple times at each sensitivity level of the control unit 22 for the irradiation start detection process. In the case where the result obtained is the result shown in FIG. 19, in which "○" indicates that there is no false detection and "x" indicates that there is false detection, the higher the sensitivity level is, the more easily the radiation image capturing apparatus 1 is influenced by the radio waves, impacts or the like and accordingly the more easily false detection occurs.

In the embodiment, the determination unit determines that a sensitivity level at which false detection (i.e. "x" in FIG. 19) does not occur at any times of the determination process is the sensitivity level at which the control unit 22 of the radiation image capturing apparatus 1 can detect start of irradiation thereof.

In the case of FIG. 19, the determination unit determines that the "low sensitivity" is the sensitivity level at which the control unit 22 of the radiation image capturing apparatus 1 can detect start of irradiation thereof (see "usable" in FIG. 19), and determines that the "high sensitivity" and the "middle sensitivity" are each not the sensitivity level at which the control unit 22 thereof can accurately detect start of irradiation thereof (see "unusable" in FIG. 19).

Application of the result of the determination process performed by the determination unit is various, as with each application described in the first embodiment.

For example, a sensitivity level determined as a sensitivity level at which the control unit 22 of the radiation image capturing apparatus 1 can detect start of irradiation thereof may be notified to an operator. The sensitivity level may be notified through an indication (message) of "Set the sensitivity for the irradiation start detection process to the low sensitivity in this radiography room." displayed on a display unit of the computer which constitutes the determination unit, a sound/voice or the like.

Instead of or in addition to the notification, the determination unit may automatically set the sensitivity level (the "low sensitivity" in the case of FIG. 19), which is determined as the sensitivity level at which the control unit 22 of the radiation image capturing apparatus 1 can detect start of irradiation thereof, to the radiation image capturing apparatus 1.

In this case, for example, the determination unit sends to the radiation image capturing apparatus 1 a signal to change the sensitivity for the irradiation start detection process to the sensitivity level to be set (the "low sensitivity" in the case of FIG. 19), and the control unit 22 of the radiation image capturing apparatus 1 changes the sensitivity in accordance with the information on the sensitivity included in the received signal.

[Advantageous Effects]

As described above, according to the radiation image capturing apparatus 1 of the third embodiment, before radiation image capturing, how much the radio waves emitted, for example, from an apparatus or the like in a radiography room or the impacts or the like added to the radiation image capturing apparatus 1 from an apparatus used for radiation image capturing influence the irradiation start detection process performed by the control unit 22 of the radiation image capturing apparatus 1 can be found in advance, and a sensitivity level at which the control unit 22 thereof can accurately detect start of irradiation thereof can be found in advance.

On the basis of the information on the sensitivity, an operator or the determination unit can change the sensitivity of the control unit 22 for the irradiation start detection process to the found sensitivity level. Accordingly, the radiation image capturing apparatus 1 can be appropriately adjusted in accordance with the operating environment of the radiation image capturing apparatus 1, and accordingly accurately detect start of irradiation thereof and appropriately perform radiation image capturing.

Consequently, for example, the following problem can be prevented from arising; the radiation image capturing apparatus 1 falsely detects start of irradiation thereof and hence needs to perform radiation image capturing again or cannot perform radiation image capturing smoothly. Accordingly, the radiation image capturing system 50 is easy to use for operators and patients as subjects and can improve its convenience.

When there are a plurality of sensitivity levels at which the control unit 22 of the radiation image capturing apparatus 1 can detect start of irradiation thereof, the determination unit selects a sensitivity level under a preset condition, such as a sensitivity level which is the highest among the usable sensitivity levels, a sensitivity level at which start of irradiation thereof can be detected in a state in which the S/N ratio is good or a sensitivity level at which power consumption in the radiation image capturing apparatus 1 is the least.

In this case, all the sensitivity levels at which the control unit 22 of the radiation image capturing apparatus 1 can detect start of irradiation thereof may be notified to an operator so that the operator selects an appropriate sensitivity level.

[Elimination of Influence of Radio Waves, Impacts, Etc. In Integration]

Even under the operating environment where the influence of the radio waves, impacts or the like exists as described above, there is a case where the sensitivity for the irradiation start detection process needs to be increased for radiation image capturing because the dose rate at which the radiation is emitted to the radiation image capturing apparatus 1 is low.

When the dose rate at which the radiation emitted to the radiation image capturing apparatus 1 is low, and the calculus of finite differences (detection method A) is adopted, the difference $\Delta d(z)$ calculated from the leak data dleak or the like read out when the radiation image capturing apparatus 1 is irradiated may be smaller than the difference $\Delta d(z)$ which is large due to the influence of the radio waves, impacts or the like, and accordingly it may be difficult to detect start of irradiation of the radiation image capturing apparatus 1 even when the threshold $\Delta$dth is adjusted.

In such a case, in the embodiment, start of irradiation thereof is detected by using the integration (detection method B). However, as described above, the integration is a method of integrating (adding up) the differences $\Delta d(z)$ over time to calculate the integrated value $\Sigma\Delta d$. Hence, under the operating environment where the influence of the radio waves, impacts or the like exists, the differences $\Delta d(z)$ which are large due to the influence of the radio waves, impacts or the like are integrated one after another.

If no limit is put on the differences $\Delta d(z)$ and accordingly the differences $\Delta d(z)$ are simply integrated under the operating environment where the influence of the radio waves, impacts or the like exists, the integrated value $\Sigma\Delta d$ of the differences $\Delta d(z)$ gradually becomes large although the radiation image capturing apparatus 1 is not irradiated. Then, at one point of time, the integrated value $\Sigma\Delta d$ is equal to or more than the threshold $\Sigma\Delta$dth, and accordingly start of irradiation of the radiation image capturing apparatus 1 is falsely detected.

Under such an operating environment, the difference $\Delta d(z)$ calculated from the leak data dleak or the like read out at the time of irradiation thereof is smaller than the difference(s) $\Delta d(z)$ which is large due to the influence of the radio waves, impacts or the like. Hence, by using that fact, the following is configured in order to eliminate the influence of the radio waves, impacts or the like in the integration.

Figure 20:
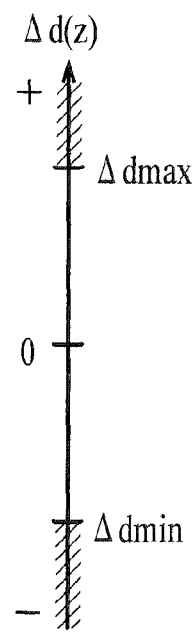
FIG. 20 is an illustration for explaining the upper limit and the lower limit of the difference, the values (differences) of which are integrated in the integration in a third embodiment.

That is, on the differences $\Delta d(z)$ to be integrated in the integration, the upper limit $\Delta$dmax and the lower limit $\Delta$dmin, for example, shown in FIG. 20 may be set. Then, only the differences $\Delta d(z)$ each of which is equal to or more than the lower limit $\Delta$dmin and equal to or less than the upper limit $\Delta$dmax are integrated. In other words, the differences $\Delta d(z)$ each of which is less than the lower limit $\Delta$dmin or more than the upper limit $\Delta$dmax (see shaded portions in FIG. 20) are not integrated.

The upper limit $\Delta$dmax and the lower limit $\Delta$dmin may be set in such a way that the absolute value of the upper limit $\Delta$dmax and the absolute value of the lower limit $\Delta$dmin are the same or different.

With this configuration, the differences $\Delta d(z)$ (the absolute values of the differences $\Delta d(z)$, to be accurate) each of which is large due to the influence of the radio waves, impacts or the like are each more than the upper limit $\Delta$dmax or less than the lower limit $\Delta$dmin. In other words, the fluctuation of the difference $\Delta d(z)$ which is large due to the influence thereof is wider than a numerical value range defined by the upper limit $\Delta$dmax and the lower limit $\Delta$dmin.

In other words, the upper limit $\Delta$dmax and the lower limit $\Delta$dmin in the integration are each set to define a numerical value range which is narrower than the fluctuation of the difference $\Delta d(z)$ which is large due to the influence of the radio waves, impacts or the like.

Thus, the differences $\Delta d(z)$, the absolute values of which are large due to the influence of the radio waves, impacts or the like are not integrated in the integration, and accordingly the integrated value $\Sigma\Delta d$ of the differences $\Delta d(z)$ being equal to or more than the threshold $\Sigma\Delta$dth although the radiation image capturing apparatus 1 is not irradiated can be prevented.

Further, in the integration, the differences $\Delta d(z)$ without the influence of the radio waves, impacts or the like are integrated. Accordingly, even when the dose rate at which the radiation is emitted to the radiation image capturing apparatus 1 is low under the operating environment where the influence of the radio waves, impacts or the like exists, the integrated value $\Sigma\Delta d$ of the differences $\Delta d(z)$ can be equal to or more than the threshold $\Sigma\Delta$dth without the influence thereof, and accordingly the radiation image capturing apparatus 1 can accurately detect start of irradiation thereof and appropriately perform radio image capturing.

In the integration, it is possible that when the differences $\Delta d(z)$ are integrated, noise is integrated too, and hence although the radiation image capturing apparatus 1 is not irradiated, the integrated value $\Sigma\Delta d$ of the differences $\Delta d(z)$ is equal to or more than the threshold $\Sigma\Delta$dth, and accordingly start of irradiation thereof is falsely detected.

Figure 21:
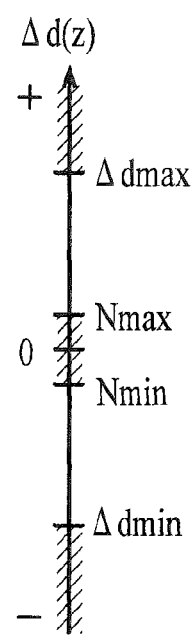
FIG. 21 is an illustration for explaining a numerical value range of the difference regarded as noise in FIG. 20.

Hence, for example, when the upper limit $\Delta$dmax and the lower limit $\Delta$dmin are set on the differences $\Delta d(z)$ to be integrated in the integration as described above, for example, as shown in FIG. 21, a numerical value range to eliminate noise, namely, the numerical value range defined by Nmin and Nmax shown in FIG. 21, may be set around the difference $\Delta d(z)=0$ too. Then, the differences $\Delta d(z)$ each of which is within the numerical value range defined by Nmin and Nmax (see shaded portions in FIG. 21) are regarded as noise and are not integrated.

With this configuration, as described above, the influence of the radio waves, impacts or the like is eliminated, and the differences $\Delta d(z)$ without the influence thereof are integrated, and accordingly start of irradiation of the radiation image capturing apparatus 1 can be accurately detected. In addition, the integrated value $\Sigma\Delta d$ being equal to or more than the threshold $\Sigma\Delta$dth due to the integration of noise can be prevented, and accordingly false detection of start of irradiation of the radiation image capturing apparatus 1 due to the integration of noise can be prevented for sure.

It is needless to say that the present invention is not limited to the above-described embodiments but can be appropriately modified without departing from the spirit of the present invention.

This application is based upon and claims the benefit of priority under 35 USC 119 of Japanese Patent Application No. 2012-239783 filed on Oct. 31, 2012, the entire disclosure of which, including the description, claims, drawings and abstract, is incorporated herein by reference in its entirety.

What is claimed is:

1. An x-ray radiation image capturing system comprising:
   an x-ray radiation image capturing apparatus including:
   a plurality of scan lines;
   a plurality of signal lines disposed to intersect with the scan lines;

a plurality of x-ray radiation detection elements disposed two-dimensionally;

a scan driving unit which applies ON voltage and OFF voltage to the scan lines, switching the ON voltage and the OFF voltage;

a plurality of switch elements which are connected to the scan lines and release electric charges accumulated in the x-ray radiation detection elements to the signal lines when the ON voltage is applied to the switch elements via the scan lines;

a readout integrated circuit which reads out the electric charges released from the x-ray radiation detection elements as image data; and a control unit which controls the scan driving unit and the readout integrated circuit since before start of irradiation of the x-ray radiation image capturing apparatus and detects the start of the irradiation when data read out by the readout integrated circuit is equal to or more than a threshold; and one or more x-ray radiation generation apparatuses each of which irradiates the x-ray radiation image capturing apparatus; and a calculation unit which, before x-ray radiation image capturing, calculates a maximum body thickness for each of the one or more x-ray radiation generation apparatuses on the basis of the data read out in the x-ray radiation image capturing apparatus irradiated by the respective x-ray radiation generation apparatus, the maximum body thickness up to which the control unit can detect the start of the irradiation through a subject.

2. The x-ray radiation image capturing system according to claim 1, wherein the calculation unit calculates the maximum body thickness in relation to a radiography condition set to the respective x-ray radiation generation apparatus to find a relationship between the maximum body thickness and the radiography condition.

3. The x-ray radiation image capturing system according to claim 2, wherein the radiography condition includes a tube voltage supplied to the respective x-ray radiation generation apparatus.

4. The x-ray radiation image capturing system according to claim 2, wherein the calculation unit finds the relationship for the x-ray radiation image capturing apparatus with a grid attached and the x-ray radiation image capturing apparatus with no grid attached.

5. The x-ray radiation image capturing system according to claim 2 further comprising:

a console into which a desired radiography condition to be set to the respective x-ray radiation generation apparatus is input; and a notifying unit which notifies a found maximum body thickness based on the relationship between the maximum body thickness and the desired radiography condition, the found maximum body thickness up to which the control unit can detect the start of the irradiation through the subject under the radiography condition input into the console.

6. The x-ray radiation image capturing system according to claim 2 further comprising a notifying unit which (i) obtains a body thickness of the subject as a target for the x-ray radiation image capturing and (ii) notifies a found radiography condition based on the relationship between the maximum body thickness and the radiography condition, the found radiography condition under which the control unit can detect the start of the irradiation through the subject having the body thickness.

7. The x-ray radiation image capturing system according to claim 2 further comprising a notifying unit which (i) obtains a body thickness of the subject as a target for the x-ray radiation image capturing and (ii) automatically sets to the x-ray radiation image capturing apparatus a found radiography condition based on the relationship between the maximum body thickness and the radiography condition, the found radiography condition under which the control unit can detect the start of the irradiation through the subject having the body thickness.

8. The x-ray radiation image capturing system according to claim 1 further comprising a computer including a display unit, wherein information on the maximum body thickness is displayed on the display unit.

9. The x-ray radiation image capturing system according to claim 1, wherein, in addition to the maximum body thickness, the calculation unit calculates for each of the x-ray radiation generation apparatuses a minimum area of a direct irradiation region where the x-ray radiation image capturing apparatus is directly irradiated by the respective x-ray radiation generation apparatus not through the subject, the minimum area down to which the control unit can detect the start of the irradiation with the direct irradiation region.

10. The x-ray radiation image capturing system according to claim 1, wherein the control unit changes sensitivity of the control unit for an irradiation start detection process to detect the start of the irradiation by changing the threshold, and the calculation unit calculates the maximum body thickness for each of sensitivity levels of the sensitivity.

11. The x-ray radiation image capturing system according to claim 1, wherein the calculation unit performs a calculation process to calculate the maximum body thickness for each of the x-ray radiation generation apparatuses on the basis of data of a dose rate detected by a dosimeter (i) disposed at a position where the x-ray radiation image capturing apparatus is to be disposed and (ii) irradiated by the respective x-ray radiation generation apparatus instead of performing the calculation process on the basis of the data read out in the x-ray radiation image capturing apparatus irradiated by the respective x-ray radiation generation apparatus.

12. An x-ray radiation image capturing system comprising:

an x-ray radiation image capturing apparatus including:

a plurality of scan lines;

a plurality of signal lines disposed to intersect with the scan lines;

a plurality of x-ray radiation detection elements disposed two-dimensionally;

a scan driving unit which applies ON voltage and OFF voltage to the scan lines, switching the ON voltage and the OFF voltage;

a plurality of switch elements which are connected to the scan lines and release electric charges accumulated in the x-ray radiation detection elements to the signal lines when the ON voltage is applied to the switch elements via the scan lines;

a readout integrated circuit which reads out the electric charges released from the x-ray radiation detection elements as image data; and a control unit which controls the scan driving unit and the readout integrated circuit since before start of irradiation of the x-ray radiation image capturing apparatus and detects the start of the irradiation when data read out by the readout integrated circuit is equal to or more than a threshold; and an x-ray radiation generation apparatus which irradiates the x-ray radiation image capturing apparatus, wherein the control unit of the x-ray radiation image capturing apparatus is configured to change sensitivity of the control unit for an irradiation start detection process to detect the start of the irradiation by changing the threshold, and the x-ray radiation image capturing system further comprises a determination unit which, before x-ray radiation image capturing, determines whether or not the control unit can detect the start of the irradiation at each of sensitivity levels of the sensitivity on the basis of the data read out in the x-ray radiation image capturing apparatus not irradiated by the x-ray radiation generation apparatus and notifies a result of the determination.

13. The x-ray radiation image capturing system according to claim 12, wherein, with or without the notification of the result of the determination, the determination unit automatically sets to the x-ray radiation image capturing apparatus a sensitivity level determined as a sensitivity level at which the control unit can detect the start of the irradiation.

\* \* \* \* \*